(12) United States Patent
Ellies

(10) Patent No.: US 11,807,681 B2
(45) Date of Patent: *Nov. 7, 2023

(54) METHODS OF ALTERING BONE GROWTH BY ADMINISTRATION OF SOST OR WISE ANTAGONIST OR AGONIST

(71) Applicant: OSSIFI-MAB LLC, Overland Park, KS (US)

(72) Inventor: Debra L Ellies, Kansas City, KS (US)

(73) Assignee: OSSIFI-MAB LLC, Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,569

(22) Filed: Mar. 20, 2023

(65) Prior Publication Data

US 2023/0226086 A1      Jul. 20, 2023

Related U.S. Application Data

(60) Division of application No. 15/269,022, filed on Sep. 19, 2016, now Pat. No. 11,608,373, which is a continuation of application No. 14/504,544, filed on Oct. 2, 2014, now abandoned, which is a continuation of application No. 13/796,530, filed on Mar. 12, 2013, now Pat. No. 8,877,196, which is a division of application No. 13/420,846, filed on Mar. 15, 2012, now abandoned, which is a continuation of application No. 11/962,522, filed on Dec. 21, 2007, now Pat. No. 8,178,099.

(60) Provisional application No. 60/882,642, filed on Dec. 29, 2006.

(51) Int. Cl.
| | | |
|---|---|---|
| A61K 31/59 | (2006.01) | |
| A61K 38/18 | (2006.01) | |
| A61K 39/395 | (2006.01) | |
| A61K 45/06 | (2006.01) | |
| C07K 16/22 | (2006.01) | |
| A61L 27/12 | (2006.01) | |
| A61L 27/54 | (2006.01) | |
| A61K 31/66 | (2006.01) | |
| A61K 31/7088 | (2006.01) | |
| A61K 31/713 | (2006.01) | |
| A61K 38/17 | (2006.01) | |
| A61P 19/08 | (2006.01) | |

(52) U.S. Cl.
CPC ............. *C07K 16/22* (2013.01); *A61K 31/59* (2013.01); *A61K 31/66* (2013.01); *A61K 31/7088* (2013.01); *A61K 31/713* (2013.01); *A61K 38/1709* (2013.01); *A61K 38/1875* (2013.01); *A61K 39/395* (2013.01); *A61K 39/3955* (2013.01); *A61K 45/06* (2013.01); *A61L 27/12* (2013.01); *A61L 27/54* (2013.01); *A61L 2300/256* (2013.01); *A61L 2300/432* (2013.01); *A61L 2430/02* (2013.01); *A61P 19/08* (2018.01); *C07K 2317/24* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,631,211 | A | 12/1986 | Houghten |
| 4,816,567 | A | 3/1989 | Cabilly et al. |
| 4,935,496 | A | 6/1990 | Kudo et al. |
| 4,946,778 | A | 8/1990 | Ladner et al. |
| 5,010,175 | A | 4/1991 | Rutter et al. |
| 5,118,667 | A | 6/1992 | Adams et al. |
| 5,225,539 | A | 7/1993 | Winter |
| 5,298,852 | A | 3/1994 | Meyer |
| 5,324,819 | A | 6/1994 | Oppermann et al. |
| 5,344,654 | A | 9/1994 | Rueger et al. |
| 5,468,845 | A | 11/1995 | Oppermann et al. |
| 5,502,167 | A | 3/1996 | Waldmann et al. |
| 5,510,370 | A | 4/1996 | Hock |
| 5,530,101 | A | 6/1996 | Queen et al. |

(Continued)

FOREIGN PATENT DOCUMENTS

| | | |
|---|---|---|
| EP | 0162510 A1 | 11/1985 |
| EP | 0635270 A1 | 1/1995 |

(Continued)

OTHER PUBLICATIONS ("First Launch of Lilly's Evista in the USA," www.thepharmaletter.com/article/first-launch-of-lilly-s-evista-in-USA; accessed Apr. 9, 2021).
(www.accessdata.fda.gov/drugsatfda_docs/nda/2002/21-318_Forteo.cfm; accessed Apr. 9, 2021).
(www.accessdata.fda.gov/drugsatfda_docs/nda/98/20835_Actonel.cfm).
Abatangelo, et al, The frequent mutation Gly/Asp in CDR1H may determine a cross-reactive idiotope in anti-l cold agglutinins, Clin. Exp. Immunol., 104(1): 185-190 (1996).
Al Qaraghuli et al. (2020, Nature Scientific Reports 10:13969).

(Continued)

*Primary Examiner* — Elizabeth C. Kemmerer
(74) *Attorney, Agent, or Firm* — Goodwin Procter LLP

(57) ABSTRACT

The present invention provides a method of promoting local bone growth by administering a therapeutic amount of a Sost antagonist to a mammalian patient in need thereof. Preferably, the Sost antagonist is an antibody or FAB fragment selectively recognizing any one of SEQ ID NOS: 1-23. The Sost antagonist may be coadministered together or sequentially with a matrix conducive to anchoring new bone growth. Orthopedic and Periodontal devices comprising an implantable portion adapted to be permanently implanted within a mammalian body and bearing an external coating of a Sost antagonist are also disclosed, as it a method of increasing bone density by administering to a mammalian patient a therapeutic amount of a Sost antagonist together with an antiresorptive drug.

30 Claims, No Drawings

(56) References Cited

U.S. PATENT DOCUMENTS

| | | |
|---|---|---|
| 5,550,134 A | 8/1996 | Audia et al. |
| 5,558,864 A | 9/1996 | Bendig et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,656,593 A | 8/1997 | Kuberasampath et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,733,743 A | 3/1998 | Johnson et al. |
| 5,750,078 A | 5/1998 | Shitara et al. |
| 5,770,403 A | 6/1998 | Dalie et al. |
| 5,939,039 A | 8/1999 | Sapieszko et al. |
| 5,989,334 A | 11/1999 | Dry |
| 6,190,412 B1 | 2/2001 | Lee et al. |
| 6,190,880 B1 | 2/2001 | Israel et al. |
| 6,395,511 B1 | 5/2002 | Brunkow et al. |
| 6,426,332 B1 | 7/2002 | Rueger et al. |
| 6,489,445 B1 | 12/2002 | Brunkow et al. |
| 6,949,251 B2 | 9/2005 | Dalal et al. |
| 7,156,880 B2 | 1/2007 | Evans et al. |
| 7,189,263 B2 | 3/2007 | Erbe et al. |
| 7,332,276 B2 | 2/2008 | Sutherland et al. |
| 7,572,899 B2 | 8/2009 | Brunkow et al. |
| 7,578,999 B2 | 8/2009 | Winkler et al. |
| 7,968,301 B2 | 6/2011 | Krumlauf et al. |
| 8,003,108 B2 | 8/2011 | Lu et al. |
| 8,173,125 B2 | 5/2012 | Krumlauf et al. |
| 8,178,099 B2 * | 5/2012 | Ellies ............... A61P 19/08 424/178.1 |
| 8,877,196 B2 * | 11/2014 | Ellies ............... A61P 43/00 424/139.1 |
| 8,895,540 B2 | 11/2014 | DiMauro et al. |
| 9,334,331 B2 | 5/2016 | Igawa et al. |
| 10,421,807 B2 | 9/2019 | Gonzales et al. |
| 11,608,373 B2 * | 3/2023 | Ellies ............... A61K 31/7088 |
| 2002/0169122 A1 | 11/2002 | Majumdar et al. |
| 2002/0187104 A1 | 12/2002 | Li et al. |
| 2003/0039654 A1 * | 2/2003 | Kostenuik ......... A61K 47/6425 514/16.7 |
| 2003/0229041 A1 | 12/2003 | Sutherland et al. |
| 2004/0002770 A1 | 1/2004 | King et al. |
| 2004/0009535 A1 | 1/2004 | Brunkow et al. |
| 2004/0023322 A1 | 2/2004 | Goodheart |
| 2004/0023356 A1 | 2/2004 | Krumlauf et al. |
| 2004/0235728 A1 | 11/2004 | Stoch et al. |
| 2005/0256047 A1 | 11/2005 | Vignery et al. |
| 2006/0030523 A1 | 2/2006 | Wu et al. |
| 2006/0094656 A1 | 5/2006 | Vignery et al. |
| 2006/0165799 A1 | 7/2006 | Kim et al. |
| 2006/0177475 A1 | 8/2006 | Rueger et al. |
| 2006/0178752 A1 | 8/2006 | Yaccarino et al. |
| 2006/0188542 A1 | 8/2006 | Bobyn et al. |
| 2006/0188544 A1 | 8/2006 | Saito |
| 2006/0198863 A1 | 9/2006 | DePaula |
| 2006/0204542 A1 | 9/2006 | Zhang et al. |
| 2006/0246060 A1 | 11/2006 | Nesta |
| 2006/0252724 A1 | 11/2006 | Lyons et al. |
| 2006/0286103 A1 * | 12/2006 | Kolhe ............... C07K 16/06 424/143.1 |
| 2006/0293667 A1 | 12/2006 | Vignery et al. |
| 2007/0060590 A1 | 3/2007 | Shoda et al. |
| 2007/0072797 A1 | 3/2007 | Robinson et al. |
| 2007/0110747 A1 | 5/2007 | Paszty et al. |
| 2007/0172479 A1 | 7/2007 | Warne et al. |
| 2007/0292444 A1 | 12/2007 | Krumlauf et al. |
| 2007/0298038 A1 | 12/2007 | Krumlauf et al. |
| 2008/0051343 A1 | 2/2008 | Vignery et al. |
| 2008/0057051 A1 | 3/2008 | Vignery et al. |
| 2009/0130113 A1 | 5/2009 | Kneissel et al. |
| 2013/0209474 A1 | 8/2013 | Krumlauf et al. |

FOREIGN PATENT DOCUMENTS

| | | |
|---|---|---|
| EP | 1133558 A1 | 9/2001 |
| EP | 2139507 A1 | 1/2010 |
| EP | 2144613 A2 | 1/2010 |
| EP | 2586796 A1 | 5/2013 |
| EP | 3345607 B1 | 10/2022 |
| JP | 0769920 A | 3/1995 |
| JP | 2004-123610 A | 4/2004 |
| JP | 2005-519067 A | 6/2005 |
| JP | 2005-525312 A | 8/2005 |
| JP | 2006-320442 A | 11/2006 |
| JP | 61-33117 B2 | 5/2017 |
| JP | 6-511233 B2 | 5/2019 |
| WO | WO-1992/19262 A1 | 11/1992 |
| WO | WO-1994/06416 A1 | 3/1994 |
| WO | WO-2000/032773 A1 | 6/2000 |
| WO | WO-03/039534 A1 | 5/2003 |
| WO | WO-2003/061690 A1 | 7/2003 |
| WO | WO-2003/073991 A2 | 9/2003 |
| WO | WO-2003/106657 A2 | 12/2003 |
| WO | WO-2005/003158 A2 | 1/2005 |
| WO | WO-2005/014650 A2 | 2/2005 |
| WO | WO-2005/112864 A2 | 12/2005 |
| WO | WO-2005/118636 A2 | 12/2005 |
| WO | WO-2006/047310 A2 | 5/2006 |
| WO | WO-2006/102070 A2 | 9/2006 |
| WO | WO-2006/119062 A2 | 11/2006 |
| WO | WO-2006/119107 A2 | 11/2006 |
| WO | WO-2007/030616 A2 | 3/2007 |
| WO | WO-2007/061889 A2 | 5/2007 |
| WO | WO-2008/115732 A2 | 9/2008 |
| WO | WO-2008/133618 A1 | 11/2008 |
| WO | WO-2008/133722 A2 | 11/2008 |
| WO | WO-2009/039175 A2 | 3/2009 |
| WO | WO-2009/131553 A2 | 10/2009 |

OTHER PUBLICATIONS

Alaee et al, "Evaluation of the Effects of Systemic Treatment with a Scleroslin Neutralizing Antibody on Bone Repair in a Rat Femoral Defect Model" J. Ortho. Res. 32:197-203 (2014).

Albertsen, et al, "A physical map and candidate genes in the BRCA1 region on chromosome 17q12-12", Nature Genetics, vol. 7 (1994) 472-79.

Alves, et al., "Sclerosteosis: A Marker of Dutch Ancestry?", Rev. Brasil. Genet., vol. 4 (1982) 825-34.

Amgen presents denosumab and sclerostin antibody data at American Society for Bone and Mineral Research Annual Meeting. Amgen Media Press Release. <www.amgen.com/media/media_pr_detail.jsp?releaseID=907028> (2006).

Anonymous, UCB on track. UCB News <http://hugin.info/133973/R/1176122/233395.pdf> (2007).

Anonymous: "NCT01575834: Efficacy and Safety of Romosozumab Treatment in Postmenopausal Women With Osteoporosis (FRAME)", Clinicaltrials.gov, Apr. 12, 2012. [Retrieved on Aug. 12, 2019] Retrieved from the internet: https://clinicaltrials.gov/ct2/show/NCT01575834?term=NCT01575834&rank=1.

Anonymous: "NCT01631214: Study to Determine the Efficacy and Safety of Romosozumab in the Treatment of Postmenopausal Women With Osteoporosis (ARCH)", Clinicaltrials.gov, Jun. 29, 2012. [Retrieved on Aug. 12, 2019] Retrieved from the internet: https://clinicaltrials.gov/ct2/show/record/NCT01631214?term=NCT01631214&rank=1.

ASBMR 31st Annual Meeting, Presentation 1063, Sep. 15, 2009, 2 pages.

ASBMR 31st Annual Meeting, Presentation 1290, Sep. 15, 2009, 4 pages.

Atkins et al., Sclerostin Is a Locally Acting Regulator of Late-Osteoblast/Preosteocyte Differentiation and Regulates Mineralization Through a MEPE-ASARM-Dependent Mechanism, Bone Miner Res., 26(7): 1425-1436 (Jul. 2011).

Atkinson, et al., Journal of Bone and Mineral Research, vol. 20, No. 9, Suppl. 1 (2005) S294 [SU453].

Avsian-Kretchmer et al., Comparative genomic analysis of the eight-membered ring cystine knot-containing bone morphogenetic protein antagonists. Molec. Endocrinol., 18(1):1-12 (2004).

(56) References Cited

OTHER PUBLICATIONS

Babcook et al., A novel strategy for generating monoclonal antibodies from single, isolated lymphocytes producing antibodies of defined specificities. Proc. Natl. Acad. Sci. USA, 93:7843-8 (1996).
Balemans, et al., "Increased bone density in sclerosteosis is due to the deficiency of a novel secreted protein (SOST)", Human Molecular Genetics, vol. 10, No. 5, (2001) 537-43.
Balesman, et al., "Extracellular Regulation of BMP Signaling in Vertebrates: A Cocktail of Modulators", Developmental Biology., vol. 250 (2002) 231-50.
Balesman, et al., "Localization of the Gene for Sclerosteosis to the van Buchem Disease—Gene Region on Chromosome 17q12-q21", Am. J. Hum. Genet., vol. 64 (1999) 1661-69.
Baron & Rawadi, "Minireview: Targeting the Wnt/B-Catenin Pathway to Regulate Bone Formation in the Adult Skeleton" Endocrinol. 148(6) 2635-2643 (2007).
Bateman et al., Granulins: The structure and function of an emerging family of growth factors. J. Endocrinol., 158: 45-51 (1998).
Baxevanis (Ed.) et al., Bioinformatics: A practical guide to the analysis of genes and proteins, John Wiley & Sons, Inc. p. 234 (1998).
Beighton et al., Heterozygous manifestations in the heritable disorders of the skeleton. Pediatr. Radial., 27: 397-401 (1997). http://www.ncbi.nlm.nih.gov/pubmed/9133350.
Beighton, et al., "The syndromic status of sclerosteosis and van Buchem disease", Clinical Genetics, vol. 25 (1984) 175-81.
Bendayan, Possibilities of false immunocytochemical results generated by the use of monoclonal antibodies: The example of the anti-proinsulin antibody. J. Histochem. Cytochem., 43(9): 881-6 (1995).
Bergfeld et al., Release of ATP from human erythrocytes in response to a brief period of hypoxia and hypercapnia. Cardiovascular Res., 26: 40-7 (1992). http://cardiovascres.oxfordjournals.org/content/26/1/40.long.
Berman et al., The protein data bank. Acta. Cryst, 58(1):899-907 (2002).
Berzofsky, "Intrinsic and Extrinsic Factors in Protein Antigenic Structure", Science, 229(4717): 932-40 (1985).
Birren et al., EMBL sequence database accession No. AC003098.2, Nov. 14, 1997.
Bishop (Ed.), Guide to Human Genome Computing, Second Edition, Academic Press, Chapter 1: Introduction to riuman genome computer via the world wide web, pp. 1-14 (2003).
Black, D., et al. "The Effects of Parathyroid Hormone and Alendronate Alone or in Combination in Postmenopausal Osteoporosis", The New England Journal of Medicine, Sep. 25, 2003, vol. 349, Issue 13: pp. 1207-1215.
Black, et al., "A Somatic Cell Hybrid Map of the Long Arm of Human Chromosome 17, Containing the Familial Breast Cancer Locus (BRCAI)", Am. J_ Hum. Genet., vol. S2 (1993) 702-10.
Black, et al., The effects of parathyroid hormone and alendronate alone or in combination in post menopausal osteoporosis, New Eng. J. Med., 349(13): 1207-15 (2003).
Boden et al., Glucocorticoid-induced differentiation of fetal rat calvarial osteoblasts is mediated by bone morphogenetic protein-6. Endocrinology, 138(7): 2820-8 (1997).
Bonaldo et al., EMBL Sequence Database Accession No. AI113131, Sep. 4, 1998.
Bonaldo et al., Normalization and subtraction: Two approaches to facilitate gene discovery. Genome Res., 6(9): 1791-806 (1996).
Bondestam, Ligands & Signaling Components of the Transforming Growth Factor, Helsinki University Biomedical Dissertations (2002).
Bork, et al., "Go hunting in sequence databases but watch out for the traps", Trends in Genetics, vol. 12, No. 10 (1996) 425-27.
Bos et al., Ras ongogenes in human cancer: A review. Cancer Res., 49: 4682-9 (1989).
Bostrom et al., Ligand and signaling components of the transforming growth factor β family. J. Orth. Res., 13: 357-67 1995).
Bottcher et al., NCBI Sequence database accession No. NM_004329, Aug. 2, 2009.

Bouffard, et al., "A Physical Map of Human Choromosome 7: An Integrated YAC Contig Map with Average STS Spacing of 79 kb", Genome Research, vol. 7 (1997) 673-92.
Bowie et al., A method to identify protein sequences that fold into a known three-dimensional structure. Science, 253: 164-70 (1991).
Bowie et al., Deciphering the message in protein sequences: Tolerance to amino acid substitutions. Science, 247 (4948): 1306-10 (1990).
Brandao-Burch et al., Acidosis inhibits bone formation by osteoblasts in vitro by preventing mineralization. Calcif. Tissue Int., 77: 167-74 (2005).
Brenner et al., Population statistics of protein structures: Lessons from structural classifications. Curr. Op. Struct. Biol. 7(3): 369-76 (1997).
Brown, Hybridization analysis of DNA blots, Current Protocols in Protein Science, 2.10.1-2.10.16 (2000).
Brunkow, et al., "Bone Dysplasia Sclerosteosis Results from Loss of the SOST Gene Product, a Novel Cystine Knot-Containing Protein", Am. J_ Hum. Genet., vol. 68 (2001) 577-89.
Butcher et al., Increased salt concentration reversibly destabilizes p53 quaternary structure and sequence-specific DNA binding. Biochem. J., 298: 513-6 (1994).
Byrne et al., CD4+CD45RBHi T cell transfer induced colitis in mice is accompanied by osteopenia which is treatable with recombinant human osteoprotegerin. Gut, 54: 78-86 (2005).
Camacho, P., et al. "American Association of Clinical Endocrinologists and American College of Endocrinology Clinical Practice Guidelines for the Diagnosis and Treatment of Postmenopausal Osteoporosis—2016 Executive Summary", AACE/ACE Postmenopausal Osteoporosis CPG, Endocr Pract., 2016, vol. 22, Issue 9: pp. 1111-1118.
Chan, et al., "A new paradigm in the treatment of osteoporosis: Wnt pathway proteins and their antagonists", Current Opinion in Investigational Drugs, vol. 8, No. 4 (2007) 293-98.
Charlier, et al., "A pore mutation in a novel KQT-like potassium channel gene in an idiopathic epilepsy family", Nature Genetics, vol. 18 (1998) 53-5.
Chenu et al., Glutamate receptors are expressed by bone cells and are involved in bone resorption. Bone, 22(4): 295-9 (1998). http://www.ncbi.nlm.nih.gov/pubmed/9556127.
Choi et al., "Lrp4, a Novel Receptor for Dickkopf and Scleroslin, Is Expressed by Osteoblasts and Regulates Bone Growth and Turnover In Vivo" PLO/S One, vol. 4, No. 11, e7930 (2009).
Chou et al., Empirical predication of protein conformation. Ann. Rev. Biochem., 47:251-76 (1979). http://www.ncbi.nlm.nih.gov/pubmed/354496.
Clark, Antibody humanization: A case of the 'Emperor's New Clothes'?. Immunology Today, 21(8): 397-402 (2000). http://www.ncbi.nlm.nih.gov/pubmed/10916143.
Cogan et al., NCBI Sequence Database Accession No. NM 033346, Jul. 19, 2005.
Collins, "Identifying Human Disease Genes by Positional Cloning", The Harvey Lectures, Series 86 (1992) 149-64.
Collins, "Positional cloning moves from perditional to traditional", Nature Genetics, vol. 9 {1995) 347-50.
Colman, "Effects of amino acid sequence changes on antibody-antigen interactions", Research in Immunology, vol. 45 (1994) 33-6.
Cook et al., Structural basis for a functional antagonist in the transforming growth factor B superfamily. J. Biol. Chem., 80(48): 40177-86 (2005).
Cosman, F., et al. "Daily and Cyclic Parathyroid Hormone in Women Receiving Alendronate", N Engl J Med, 2005, vol. 353: pp. 566-575.
Cosman, F., et al. "Romosozumab Treatment in Postmenopausal Women with Osteoporosis", N Engl J Med, Oct. 20, 2016, vol. 375: pp. 1532-1543.
Craig et al., Sclerostin binds and regulates the activity of cysteine rich protein 61. Biochem. Biophys. Res. Commun., 293(1): 36-40 (2010).
Craig et al., Sclerostin-erbB-3 interactions: Modulation of erbB-3 activity by sclerostin. Biochem. Biophys. Res. Commun., 402: 421-4 (2010).

(56) References Cited

OTHER PUBLICATIONS

Crameri et al., DNA shuffling of a family of genes from diverse species accelerates directed evolution. Nature, 391: 288-91 (1998).

Dall'Acqua et al., Antibody humanization by framework shuffling. Methods, 36(1): 43-60 (2005). http://www.ncbi.nlm.nih.gov/pubmed/15848074.

Dawson-Hughes, B., et al. "Response to Teriparatide in Patients with baseline 25-Hydroxyvitamin D Insufficiency or Sufficiency", The Journal of Clinical Endocrinology & Metabolism, Dec. 1, 2007, vol. 92, Issue 12: pp. 4630-4636.

Declaration of Dr. Martyn Robinson, submitted in Opposition to European Patent No. 1133558, dated Jan. 13, 2008.

Declaration of Dr. Mary E. Brunkow, submitted in Opposition to European Patent No. 1133558, dated Jan. 9, 2008.

Delmas, et al., "The Use of Biochemical Markers of Bone Turnover in Osteoporosis", Osteoporosis International, Suppl 6(2000)2-17.

Deregt, et al., "Mapping of a type 1-specific and a type-common epitope on the E2 (gp53) protein of bovine viral diarrhea virus with neutralization escape mutants", Virus Research, 53(1): 81-90 (1998).

Devarajan-Ketha et al., The sclerostin-bone protein interactome, Biochemical and Biophysical Research Communications 417: 830-835 (2012).

Diez, "Skeletal effects of selective oestrogen receptor modulators (SERMS)", Human Reproduction Update, 6(3): 255-58 (2000).

Ducy et al., 5-HT and bone biology. Curr. Opin. Pharmacol., 11:34-8 (2011). http://www.ncbi.nlm.nih.gov/pubmed/21320797.

Duey et al., Genetic control of cell differentiation in the skeleton. Curr. Opin. Cell Biol., 10: 614-9 (1998). http://www.ncbi.nlm.nih.gov/pubmed/9818172.

Ebara et al., Mechanism for the action of bone morphogenetic proteins and regulation of their activity. Spine, 27(16S): S10-5 (2002). http://www.ncbi.nlm.nih.gov/pubmed/12205413.

Ebina, K., et al. "Comparison of the effects of denosumab between a native vitamin D combination and an active vitamin D combination in patients with postmenopausal osteoporosis", Journal of Bone Mineral Metabolism, Sep. 2017, vol. 35, Issue 5: pp. 571-580. (http://doi.orQ/10.1007/s00774-016-0792-5).

Edwards et al. (2003, JMB 334:103-118).

Ellies, et al., "Bone density ligand, Sclerostin, directly interacts with LRP5 but not LRP5G171V to modulate Wnt activity", Journal of Bone and Mineral Research, 21(11): 1738-49 (2006).

Expert Opinion from Dr. Catalina Lopez-Correa, submitted in Opposition to European Patent No. 1133558, dated Mar. 6, 2009.

Eyre et al., Characterization of aromatase and 17tB-hydroxysteroid dehydrogenase expression in rat osteoblastic cells. J. Bone Miner. Res., 13(6): 996-1004 (1998).

Finkelstein, "The effects of parathyroid hormone, alendronate, or both in men with osteoporosis", New Eng. J. Med., 349(13): 1216-26 (2003).

Forteo, et al., is this bone drug too good to be true? [online], Oct. 24, 2013 [retrieved Apr. 28, 2014], Retrieved from the internet <http://www.betterbones.com/osteoporosis/forteo-bonedrug.aspx>.

Fouser et al., Feedback regulation of collagen gene expression: A Trojan horse approach. Proc. Natl. Acad. Sci. USA, 88: 10158-62 (1991).

Fujiwara et al., GenBank Sequence Database Accession No. 079813, Feb. 9, 1996.

Gardner et al., Bone mineral density in sclerosteosis; Affected individuals and gene carriers. J. Clin. Endocrinol. Metab., 90(12): 6392-5 (2005).

Gavarini et al., Opposite effects of PSD-95 and MPP3 PDZ proteins on serotonin 5hydroxytryptamine2C receptor desensitization and membrane stability. Molec. Biol., 17: 461931 (2006).

Gazzerro et al., Bone morphogenetic proteins induce the expression of noggin which limits their activity in cultured rat psteoblasts_J_Clin_Invest., 102(12): 2106-14 (1998).

Gazzerro et al., Potential drug targets within bone morphogenetic protein signaling pathways. Curr. Opin. Pharmacol., 7: 325-3 (2007). http://www.ncbi.nlm.nih.gov/pubmed/17475557.

Genant, H., et al. "Effects of Romosozumab Compared With Teriparatide on Bone Density and Mass at the Spine and Hip in Postmenopausal Women With Low Bone Mass", Journal of Bone and Mineral Research, Jan. 2017, vol. 32, Issue 1: pp. 181-187.

Gencic et al., Conservative amino acid substitution in the myelin proteolipid protein of Jimpymsd mice. J. Neurosci., 10(1): 117-24 (1990).

Geriatric Medicine, vol. 44, No. 12 (2006) 1697-702.

Giannoudis el al., "Bone substitutes: An update" Injury, Int. J. Care Injured, 36S, pp. S20-S27 (2005).

Gitelman et al., Vgr-1/BMP-6 induces osteoblastic differentiation of pluripotential mesenchymal cells. Cell Growth & Differentiation, 6: 827-36 (1995).

Goel et al. (2004, J. Immunol. 173: 7358-7367).

Graner et al., Splice variants of the Drosophila PS2 integrins differentially interact with RGD containing fragments of the extracellular proteins tiggrin, Ten-m and D-Iaminin a2. J. Biol. Chem., 273(29): 18235-41 (1998).

Green et al., Cytosolic pH regulation in osteoblasts. J. Gen. Physiol., 95: 121-45 (1990).

Green et al., Antigen-specific human monoclonal antibodies from mice engineered with human Ig heavy and light chain YACs. Nat. Genet., 7:13 (1994). http://www.nature.com/ng/joumal/v7/n1/abs/ng0594-13.html.

Greene, et al., "Screening Recombinant DNA Libraries", Current Protocols in Molecular Biology, vol. 1, Chapter 6 (1990).

Gribskov et al., Profile analysis: Detection of distantly related proteins. Proc. Nat. Acad. Sci. USA, 84(13): 4355-8 (1987).

Groeneveld et al., Bone morphogenetic proteins in human bone regeneration. Eur. J. Endocrinol., 142: 9-21 (2000).

Gronthos et al., Integrin expression and function on human osteoblast-like cells. J. Bone Miner. Res., 12(8): 1189-97 (1997) http://www.ncbi.nlm.nih.gov/pubmed/9258748.

Groppe et al., Structural basis of BMP signaling inhibition by the cystine knot protein noggin. Nature, 420: 636-42 (2002) http://www.ncbi.nlm.nih.gov/pubmed/12478285.

Harlow et al., Antibodies: A Laboratory Manual, Cold Spring Harbor Laboratory, 141-157 (1988).

Harris, Processing of C-terminal lysine and arginine residues of proteins isolated from mammalian cell culture. J. Chromatogr., 705: 129-34 (1995). http://www.sciencedirect.com/science/article/pii/002196739401255D.

Hart et al., Crystal structure of the human TβR2 ectodomain-TGF-β3 complex. Nat. Struc. Biol., 9(3): 203-8 (2002).

Heaney, "Advances in therapy for osteoporosis", Clinical Medicine & Research, 1(2): 93-99 (2003).

Heinecke et al., Receptor oligomerization and beyond: A case study in bone morphogenetic proteins, BMC Biol., 7: 59 (2009).

Hill et al., Multiple extracellular signals promote osteoblast survival and apoptosis. Endocrinology, 138(9): 3849-58 (1997).

Hillier et al., EMBL Sequence Database Accession No. AA393939, May 19, 1997.

Hillier et al., GenBank Sequence Database Accession No. AA393768, Apr. 24, 1997.

Hillier, et al., "Generation and Analysis of 280,000 Human Expressed Sequence Tags", Genome Research, vol. 6 (1996) 807-28.

Hilliker et al., Truncation of the amino terminus of PTH alters its anabolic activity on bone in vivo. Bone, 19(5): 469-77 (1996). http://www.ncbi.nlm.nih.gov/pubmed/8922645.

Hock et al., Perspective: Osteoblast apoptosis and bone turnover. J. Bone Miner. Res., 16(6): 975-84 (2001). http://www.ncbi.nlm.nih.gov/pubmed/11393794.

Hoggard et al., Localization of leptin receptor mRNA splice variants in murine peripheral tissues by RT-PCR and in situ hybridization. Biochem. Biophys. Res. Commun., 232: 383-7 (1997). http://www.ncbi.nlm.nih.gov/pubmed/9125186.

Holdsworth et al., "Novel Actions of scleroslin on bone" J. Mol. Endocrinol. 62(2) 167-185 (2019).

Holdsworth, et al., "Characterization of the Interaction of Sclerostin with the Low Density Lipoprotein Receptor-related Protein (LRP) Family of Wnt Co-receptors", J Biol Chem, 287(32): 26264-77 (2012).

(56) References Cited

OTHER PUBLICATIONS

Holliger et al., Engineered antibody fragments and the rise of single domains. Nat. Biotech., 23(9): 1126-36 (2005). http://www.ncbi.nlm.nih.gov/pubmed/16151406.
Holm et al., Protein folds and families: Sequence and structure alignments. Nucl. Acid Res., 27(1): 244-7 (1999).
Holt, et al., Domain antibodies: Proteins for therapy. Trends Biotechnol., 21(11): 484-90 (2003) http://www.cell.com/trends/biotechnology/pdf/S0167-7799%2803%2900245-2.pdf.
Hoogewerf et al., Glycosaminoglycans mediate cell surface oligomerization of chemokines. Biochemistry, 36: 13570-8 (1997). http://www.ncbi.nlm.nih.gov/pubmed/9354625.
Hosking, et al., "Osteoporosis therapy: an example of putting evidence-based medicine into clinical practice", QJM: Monthly Journal of the Association of Physicians, 98(6): 403-13 (2005).
Hsu et al., The Xenopus dorsalizing factor gremlin indentified a novel family of secreted proteins that antagonize BMP activities. Molec. Cell, 1: 673-83 {1998).
http://ghr.nlm.nih.gov/gene/SOST, accessed Oct. 31, 2016.
http://pi.lilly.com/ca/forteo-ca-pm.pdf; accessed Apr. 9, 2021.
https://pubchem.ncbi.nlm.nih.gov/compound/Risedronic-acid; accessed Apr. 9, 2021.
https://www.medsafe.govt.nz/profs/Datasheet/m/miacalcicinj.pdf; accessed Apr. 9, 2021.
https://www.rxlist.com/evista-drug.htm#indications; accessed Apr. 9, 2021.
Hulley et al., Inhibition of mitogen-activated protein kinase activity and proliferation of an early osteoblast cell line (MBA 15.4) by dexamethasone: Role of protein phosphatases. Endocrinol., 139(5): 2423-31 (1998).
Huse et al., Generation of a large combinatorial library of the immunoglobulin repertoire in phage lambda. Science, 246: 1275-81 (1989).
Iemura et al., Direct binding of follistatin to a complex of bone-morphogenetic protein and its receptor inhibits ventral and epidermal cell fates in early Xenopus embryo. Proc. Natl. Acad. Sci. USA, 95: 9337-42 (1998).
Inkelstein et al., "The Effects of Parathyroid Hormone, Alendronate, or Both in Men with Osteoporosis" N Engl J Med. vol. 349, 1216-1226 (2003).
Innis et al., Evolutionary trace analysis of TGF-B and related growth factors: Implications for stie-directed mutagenesis. Protein Engineering, 13(12): 839-47 (2000).
Jakobovits et al., Production of antigen-specific human antibodies from mice engineered with human heavy and light chain YACsa. Ann. NY. Acad. Sci., 764: 525-35 (1995).
Jee et al., Overview: Animal models of osteopenia and osteoporosis. J. Musculoskel. Neuron. Interact., 1: 193-207 (2001).
Jilka et al., Increased bone formation by prevention of osteoblast apoptosis with parathyroid hormone. J. Clin. Invest., 104: 439-46 (1999).
Jilka et al., Osteoblast programmed cell death (apoptosis): Modulation by growth factors and cytokines. J. Bone Miner Res., 13(5): 793-802 (1998).
Jolette, J., et al. "Sclerostin Monoclonal Antibody Stimulates Bone Formation and Improves the Strength and Density of the Fracture Callus and Lumbar Spine in a Primate Fibular Osteotomy Model", Oral Presentations, Presentation No. 1290, Session: Concurrent Oral Session 47: Bone Biomechanics and Quality III, Sep. 15, 2009, Colorado Convention Center, Room 205-207.
Journal of Bone and Mineral Research, vol. 21, Suppl. 1 (2006) S72[1272].
Kamimura, M., et al. "Pretreatment of daily teriparatide enhances the increase of bone mineral density in cortical bones by denosumab therapy", Ther Clin Risk Manage., 2018, vol. 14: pp. 637-642.
Kang et al., Linkage of recognition and replication functions by assembling combinatorial antibody Fab libraries along phage surfaces. Proc. Natl. Acad Sci. USA, 88: 4363-6 (1991).
Katagiri et al., The non-osteogenic mouse pluripotent cell line, C3H10T1/2, is induced to differentiate into osteoblastic cells by recombinant human bone morphogenetic protein-2. Biochem. Biophys. Res. Comm., 172(1):2 95-9 (1990).
Kawabata et al., Signal transduction by bone morphogenetic proteins. Cytokine and Growth Factor Reviews, 9(1): 49-61 (1998).
Keaveny, T., et al. "Greater Gains in Spine and Hip Strength for Romosozumab Compared With Teriparatide in Postmenopausal Women With Low Bone Mass", Journal of Bone and Mineral Research, Sep. 2017, vol. 32, Issue 9: pp. 1956-1962.
Keller et al., Molecular recognition of BMP-2 and BMP receptor IA Nat. Struct Mol. Biol., 11(5): 481-488 (2004).
Kelly, et al., "Intercellular adhesion molecule-1-deficient mice are protected against ischemic renal injury", J. Clin. Invest., 97(4): 1056-63 (1996).
Khalil, TGF-13: From latent to active. Microbes and Infection, 1(15): 1255-63 (1999).
Khan et al. (2014, J. Immunol. 192: 5398-5405).
Khosla, et al., "Treatment options for osteoporosis", Mayo Clinic Proceedings, vol. 70, No. 10 (1995) 978-82.
Kim et al., "Sclerostin antibody administration converts bone lining cells into active osteoblasts" J. Bone Miner. Res. 32 5) 892-901 (2017).
Kim et al. "Sclerostin inhibits Wnt signaling through tandem interaction with two LRP6 ectodomains," Nature Communications, 2020, vol. 11. 46 pages.
Kirsch et al., BMP-2 antagonists emerge from alterations in the low-affinity binding epitope for receptor BMPR-11, EMBO J., 19(13): 3314-24 (2000).
Kohler, et al., "Continuous cultures of fused cells secreting antibody of predefined specificity", Nature, vol. 256 (1975) 495-97.
Koli et al., Latency, activation, and binding proteins of TGF -. Microscopy Res. Tech., 52: 354-62 (2001).
Koreth, et al., "Microsatellites and PCR Genomic Analysis", Journal of Pathology, vol. 178 (1996) 239-48.
Krause et al., Distinct modes of inhibition by sclerostin on bone morphogenetic protein and Wnt signaling pathways. J. Biol. Chem., 285(53): 41614-26 (2010).
Kunkel et al., Rapid and efficient site-specific mutagenesis without phenoypic selection. Meth. Enzymol., 154: 367-82 (1987).
Kunkel, Rapid and efficient site-specific mutagenesis without phenotypic selection. Proc. Natl. Acad. Sci. USA, 82: 488-92 (1985).
Kurahashi, et al., "Regions of genomic instability on 22q11 and 11q23 as the etiology for the recurrrent constitutional 1(11;22)", Human Molecular Genetics, vol. 9, No. 11 (2000) 1665-70.
Kusu, et al., "Sclerostin Is a Novel Secreted Osteoclast-derived Bone Morphogenetic Protein Antagonist with Unique Ligand Specificity", Journal of Biological Chemistry, vol. 278, No. 26 (2003) 24113-17.
Labat et al., Retroviral expression in mononuclear blood cells isolated from a patient with osteopetrosis (Albers-Schonberg disease). J. Bone Miner. Res., 5(5): 425-35 (1989).
Lasic, Novel applications of liposomes. Trends Biotechnol., 16(7): 307-21 (1998).
Laurencin et al., "Bone Graft Substitutes" Expert Rev. Med. Devices, vol. 3, No. 1, pp. 49-57 (2006).
Leppert, et al., "Benign familial neonatal epilepsy with mutations in two potassium channel genes", Current opinion in Neurology, vol. 12 (1999) 143-47.
Lewiecki, "Rank ligand inhibition with denosumab for the management of osteoporosis" Expert Opin. Biol. Ther., vol. 6, No. 10, pp. 1041-1050 (2006).
Li et al., "Sustained-release of sclerostin single-chain antibody fragments using poly(lactic-co-glycolic acid) microspheres for osteoporotic fracture repair" J. Biomed. Mater. Res. 1-9 (2019).
Li et al., "Targeted Deletion of the Sclerostin Gene in Mice Results in Increased Bone Formation and Bone Strength*" J. Bone Miner. Res., vol. 23, No. 6, 860-69 (2008).
Li et al., "Sclerostin Binds to LRP5/6 and Antagonizes Canonical Wnt Signaling", Journal of Biological Chemistry, vol. 280, No. 20 (2005) 19883-7.
Li et al, Increased Bone Formation and Bone Mass Induced by Sclerostin Antibody Is Not Affected by Pretreatment or Cotreatment with Alendronate in Osteopenic, Ovariectomized Rats, Endocrinology, 152(9):3312-3322 (Sep. 2011).

(56) References Cited

OTHER PUBLICATIONS

Li et.al., Treatment with an anti-sclerostin antibody directly stimulates bone formation in a dose-dependent manner in ovariectomized rats with established osteopenia. J. Bone Min. Res., 22(Suppl. S1): S65 (2007).

Lian et al., Bone Formation: Maturation and Functional Activities of Osteoblast Lineage Cells, Primer on the Metabolic Bone Diseases and Disorders of Mineral Metabolism, 5th Edition, 13-27 (2003).

Lian et al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).

Lierop et al., Van Buchem disease: Clinical, biochemical and densitometric features of patients and disease carriers. J. Bone Miner. Res. Accepted Article (2012).

Lim et al., "Profile of romosozumab and its potential in the management of osteoporosis" Drug Design, Development and Therapy, vol. 11, pp. 1221-1231 (2017).

Linear human genomic DNA from chromosome 17, EMBL Accession No. AC003098, accessed Oct. 31, 2016.

Linear mRNA EST, EMBL Accession No. AA399939, accessed Oct. 31, 2016.

Linear mRNA rat EST, EMBL Accession No. AI113131, accessed Oct. 31, 2016.

Lintern, et al., "Characterization of Wise Protein and Its Molecular Mechanism to Interact with both Wnt and BMP Signals", J. Biol. Chem., 284(34): 23159-68 (2009).

Liu et al., Human type II receptor for bone morphogenic proteins (BMPs): Extension of the two-kinase receptor model to the BMP5. Molec. Cell. Biol., 15(7): 3479-86 (1995).

Lloyd et al. (2009, Protein Engineering, Eng. Design & Selection 22(3): 159-168).

Lonberg et al., Antigen-specific human antibodies from mice comprising four distinct genetic modifications. Nature, 368: 856 (1994).

Loots et al., Genomic deletion of a long-range bone enhancer misregulates sclerostin in Van Buchem disease. Genome Res., 15: 928-35 (2005).

Low et al., Mimicking somatic hypermutation: Affinity maturation of antibodies displayed on bacteriophage using a bacterial mutator strain. J. Mol. Biol., 250: 350-68 (1996).

Lowik et al., Wnt signaling is involved in the inhibitory action of sclerostin on BMP-stimulated bone formation. J. Musculoskeleton Neuronal Interact. 6: 357 (2006).

Luckman et al., Heterocycle-containing bisphosphonates cause apoptosis and inhibit bone resorption by preventing protein prenylation: Evidence from structure-activity relationships in J774 macrophages. J. Bone Miner. Res., 13(11): 1668-78 (1998).

Luckman et al., Nitrogen-containing bisphosphonates inhibit the mevalonate pathway and prevent post-translational prenylation of GTP-binding proteins, including Ras. J. Bone Miner. Res., 13(4): 581-9 (1998).

MacDonald, et al., "Emerging therapies in osteoporosis," Clinical Rheumatology, vol. 15, No. 3 (2001) 483-96.

Matthews et al., Adenovirus protein-protein interactions: Hexon and protein VI. J. Gen. Virol, 75: 3365-74 (1994).

McClung et al., Inhibition of sclerostin with AMG 785 in postmenopausal women with low bone mineral density: Phase 2 trial results—Abstract presented at the 2012 meeting of the American Society for Bone and Mineral Research (2012).

McClung et al., Romosozumab in Postmenopausal Women with Low Bone Mineral Density, N Engl J Med, 370:412-2 (2014).

McClung, et al., "Denosumab in Postmenopausal Women with Low Bone Mineral Density", The New England Journal of Medicine, 354(8): 821-31 (2006).

McColm et al., Single- and Multiple-Dose Randomized Studies of Blosozumab, a Monoclonal Antibody Against Sclerostin, in Healthy Postmenopausal Women, Journal of Bone and Mineral Research, 29(4): 935-943 (Apr. 2014).

McGuinness, et al., "Class 1 outer membrane protein of Neisseria meningitidis: epitope analysis of the antigenic diversity between strains, implications for subtype definition and molecular epidemiology", Mol. Microbiol., vol. 7, No. 4 (1993) 505-14.

Merriam Webster's Medical Desk Dictionary (1986) 375-376.

Merriam Webster's Medical Desk Dictionary (1986) 448.

Miyazono et al., Divergence and convergence of TGF-B/BMP signaling. J. Cell. Physiol., 187: 265-76 (2001).

Morais et al., In vitro biomineralization by osteoblast-like cells I. Retardation of tissue mineralization by metal salts. Biomaterials, 19: 13-21 (1998).

Morrison et al., ATP is a potent stimulator of the activation and formation of rodent osteoclasts. J. Physiol., 511.2: 95-500 (1998).

Mosekilde et al., Assessing bone quality—Animcal models in preclinical osteoporosis research. Bone, 17(4): 343S-52S (1995).

Moult, The current state of the art in protein structure predicion. Curr. Opin. Biotech., 7(4):422-7 (1996).

Muntoni et al., A mutation in the dystrophin gene selectively affecting dystrophin expression in the heart. J. Clin. Invest, 96: 693-9 (1995).

Nagaraja, et al., "X Chromosome Map at 75-kb STS Resolution, Revealing Extremes of Recombination and GC Content", Genome Research, vol. 7 (1997) 210-22.

Nakamura, Y. et al. "Vitamin D and Calcium Are Required during Denosumab Treatment in Osteoporosis with Rheumatoid Arthritis", Nutrients, 2017, vol. 9, Issue 428: pp. 1-10.

Nakase et al., Transient and localized expression of bone morphogenetic protein 4 messenger RNA during fracture healing. J. Bone Miner. Res., 9(5): 651-9 (1994).

Nelson, "Positional cloning reaches maturity", Current Opinion in Genetics and Development, vol. 5 (1995) 298-303.

New Pharmacology (3rd ed.), (1996) 519-20.

Nickel et al., The crystal structure of the BMP-2: BMPR-1A complex and the generation of BMP-2 antagonists. J. Bone Joint Surg., 83-A:S1-7-S1-14 (2001).

Niemann-Pick Disease Type 2, OMIM (2007) 607625.

Nifuji et al., Coordinated expression of noggin and bone morphogenetic proteins (BMPs) during early skeletogenesi and induction of noggin expression by BMP-7. J. Bone Miner. Res., 14(12): 2057-66 (1999).

Nippon Rinsho (Extra) Blood purification therapy (1/2), vol. 49, (1991 Extra ed.,) 725-31.

Niu et al., Sclerostin inhibition leads to increased periosteal and endocortical bone formation as well as decreased cortical porosity in aged ovariectomized rats. J. Bone Min. Res., 22(Suppl. S1): S65 (2007).

Nordsletten et al., The neuronal regulation of fracture healing. Acta Orthop Scand., 65(3): 299-304 (1994).

Nygren et al., Scaffolds for engineering novel binding sites in proteins. Curr. Opin. Struct. Biol., 7: 463-9 (1997).

Oelgeschlager et al., The evolutionarily conserved BMP-binding protein twisted gastrulation promotes BMP signalling. Nature, 405: 757-63 (2000).

Ominsky, et al., "Sclerostin monoclonal antibody treatment increases bone strength in aged osteopenic overiectomized rats", Journal of Bone and Mineral Research, vol. 21, No. Suppl. 1 (2006) S44.

Ominsky, M., et al. "Two Doses of Sclerostin Antibody in Cynomolgus Monkeys Increases Bone Formation, Bone Mineral Density, and Bone Strength", Journal of Bone and Mineral Research, May 2010, vol. 25, Issue 5: pp. 948-959.

Oreffo et al., Human bone marrow osteoprogenitors express estrogen receptor-alpha and bone morphogenetic proteins 2 and 4 mRNA during osteoblastic differentiation. J. Cell. Biochem., 75: 382-92 (1999).

Orriss et al., Purinergic signaling and bone remodeling. Curr. Opin. Pharmacol., 10: 322-30 (2010).

Oshima et al., TGF-13 receptor type II deficiency results in defects of yolk Sac hematopoiesis and vasculogenesis. Dev. Biol., 179: 297-302 (1996).

Padhi et al., "Multiple Doses of Sclerostin Antibody Romosozumab in Healthy Men and Postmenopausal Women With Low Bone Mass: A Randomized, Double-Blind, Placebo-Controlled Study" J. Clin. Pharmacol., vol. 54, No. 2, 168-78 (2013).

(56) References Cited

OTHER PUBLICATIONS

Padhi et al., Anti-sclerostin antibody increases markers of bone formation in healthy postmenopausal women. J. Bone Min. Res., 22: S37 (2007).
Padhi et al., OC35—Effects of anti-sclerostin monoclonal antibody in healthy postmenopausal women. Osteoporosis Int., 19: Suppl. 1: S19 (2008).
Padhi, D., et al. "Single-Dose, Placebo-Controlled, Randomized Study of AMG 785, a Sclerostin Monoclonal Antibody", Journal of Bone and Mineral Research, Jan. 2011, vol. 26, Issue 1: pp. 19-26.
Padlan et al., Structure of an antibody-antigen complex; Crystal structure of the HyHEL-10 Feb-lysozyme complex. Proc. Natl. Acad. Sci. USA, 86: 5938-42 (1989).
Palokangas et al., Endocytic pathway from the basal plasma membrane to the ruffled border membrane in bone-resorbing osteoclasts. J. Cell Sci., 110: 1767-80 (1997).
Pandey, et al., "Nucleotide sequence databases: a gold mine for biologists", TIBS, vol. 24 (1999) 276-80.
Patel, "Current and potential future drug treatments for osteoporosis", Annals of Rheumatic Diseases, vol. 55 (1996) 700-714.
Patten et al., Applications of DNA shuffling to pharmaceuticals and vaccines. Curr. Opin. Biotechnol., 8: 724-33 (1997).
Pearson et al., Effective protein sequence comparison. Chapter 15, pp. 227-258 (1996).
Peerlinck, et al., "Antifactor VIII Antibody Inhibiting Allogeneic but not Autologous Factor VIII in Patients With Wild Hemophilia A", Blood, 93(7): 2267-73 (1999).
Piccolo, et al., "The head inducer Cerberus is a multifunctional antagonist of Nodal, BMP and Wnt signals", Nature, vol. 397 (6721) (1999) 707-10.
Piek et al., Specificity, diversity, and regulation of TGF-B superfamily signaling. Faseb J., 13: 2105-24 (1999).
Pietromonaco, et al., "Protein Kinase C-0 Phosphorylation of Moesin in the Actin-binding Sequence", Journal of Biological Chemistry, vol. 273, No. 13 (1998) 7594-603.
Pignatti, et al., "Tracking Disease Genes by Reverse Genetics", J. Psychiat. Res., vol. 26, No. 4 (1992) 287-98.
Pittenger et al., Multilineage potential of adult human mesenchymal stem cells. Science, 284: 143-7 (1999).
Poole, et al., "Sclerostin is a delayed secreted product of osteocytes that inhibits bone formation", FASEB Journal, vol. 19, No. 13 (2005) 1-18.
Poosarla et al. (2017, Biotechn. Bioeng. 114(6):1331-1342).
Porter, The hydrolysis of rabbit Y-globulin and antibodies with crystalline papain_Biochem. J., 73: 119-26 (1959).
Rachner et al., Osteoporosis: Now and the future. Lancet, 377(9773): 1276-87 (2011).
Rawaldi, et al., "BMP-2 Controls Alkaline Phosphatase Expression and Osteoblast Minerlization by a Wnt Autocrine Loop", Journal of Bones and Mineral Research, vol. 18, No. 10 (2003) 1842-53.
Recknor et al., The Effect of Discontinuing Treatment With Blosozumab: Follow-up Results of a Phase 2 Randomized Clinical Trial in Postmenopausal Women With Low Bone Mineral Density, Journal of Bone and Mineral Research, 30 (9): 1717-1725 (Sep. 2015).
Reddi et al., The *Escherichia coli* chaperonin 60 (groEL) is a potent stimulator of osteoclast formation. J. Bone Miner. Res., 13(8): 1260-6 (1998).
Reddi, Interplay between bone morphogenetic proteins and cognate binding proteins in bone and cartilage development: Noggin, chordin and DAN. Arthritis Res., 3(1): 1-5 (2000).
Riggs, Overview of osteoporosis. West J. Med., 154: 63-77 (1991).
Robinson et al., "Sclerostin: how human mutations have helped reveal a new target for the treatment of osteoporosis" Drug Disc. Today, vol. 18, Nos. 13-14, 637-43 (2013).
Robling, et al., "Anabolic and Catabolic Regimens of Human Parathyroid Hormones 1-34 Elicit Bone-and Envelope-Specific Attenuation of Skeletal Effects in Sost-Deficient Mice", Endocrinology, 152(8): 2963-75 (2011).
Rodan GA, Martin TJ. Therapeutic approaches to bone diseases. Science. 289(5484): 1508-14 (Sep. 2000).

Rosen, "BMP and BMP Inhibitors in Bone" Ann. NY Acad. Sci., vol. 1068, 19-25 (2006).
Rosenzweig et al., Cloning and characterization of a human type II receptor for bone morphogenetic proteins. Proc. Natl. Acad. Sci. USA, 92: 7632-7636 (1995).
Rudikoff, et al., Single amino acid substitution altering antigen-binding specificity, Proc. Natl. Acad. Sci. USA, 79: 1979-83 (1982).
Ruppert et al., Human bone morphogenetic protein 2 contains a heparin-binding site which modifies its biological activity. Eur. J. Biochem., 237: 295-302 (1996).
Saag, et al., Romosozumab or Alendronate for Fracture Prevention in Women with Osteoporosis The New England Journal of Medicine, Oct. 12, 2017, vol. 377: pp. 1417-1427.
Saini, et al., "Parathyroid Hormone (PTH)/PTH-related Peptide Type 1 Receptor (PPR) Signaling in Osteocytes Regulates Anabolic and Catabolic Skeletal Responses to Pth", J. Biol. Chem., 288(28): 20122-34 (2013).
Sambrook, et al., Molecular Cloning—a Laboratory Manual, Second Edition, "Synthetic Oligonucleotide Probes", Chapter 11 (1989) 11.1-19 and 11.58-61.
Sanger et al., DNA sequencing with chain-terminating inhibitors. Proc. Natl. Acad. Sci. USA, 74: 5463-7 (1997).
Sastry et al., Cloning of the immunological repertoire in *Escherichia coli* for generation of monoclonal catalytic ntibodies: Construction of a heavy chain variable region-specific cDNA library. Proc. Natl. Acad. Sci. USA, 86: 6728-32 (1989).
Scatchard et al., The attractions of proteins for small molecules and ions. Ann. N.Y. Acad. Sci., 51: 660-72 (1949).
Scheufler et al., Crystal structure of human bone morphogenetic protein-2 at 2.7 A resolution. J. Mol. Biol., 287(1): 01-15 (1999).
Schmitt et al., Bone morphogenetic proteins: An update on basic biology and clinical relevance. J. Orth. Res., 17: 269-78 (1999).
Schwarz, et al., "Receptor activator of nuclear kB ligand and osteoprotegerin: where are we now and what about future treatment uses?", Current Opinion in Orthopaedics, 16(5): 370-75 (2005).
Serra et al., Expression of a truncated, kinase-defective TGF-13 type II receeptor in mouse skeletal tissue promotes terminal chondrocyte differentiation and osteoarthritis. J. Cell. Biol., 139(2): 541-52 (1997).
Silverman, "Sclerostin", J. Osteoporosis, vol. 2010 (2010) Article #941419.
Siris, Clinical Review: Paget's disease of bone. J. Bone Miner. Res., 13(7): 1061-5 (1998).
Sivakumar et al., New insights into extracellular matrix assembly and reorganization from dynamic imaging of extracellular matrix proteins in living osteoblasts, J. Cell. Sci., 119(7): 1350-60 (2006).
Skjerpen et al., Binding of FGF-1 variants to protein kinase CK2 correlates with mitogenicity. EMBO J., 21(15): 4058-69 (2002).
Slater et al., Involvement of platelets in stimulating osteogenic activity_ J. Orthopaedic Res., 13: 655-63 (1995).
Smith et al., Glucocorticoids inhibit development stage-specific osteoblast cell cycle. J. Biol. Chem., 275: 19992-20001 (2000).
Smith, TGF J3 inhibitors, new and unexpected requirements in vertebrate development. TIG, 15(1): 3-5 (1999).
Sohocki et al., A range of clinical phenotypes associated with mutations in CRX, a photoreceptor transcription-factor gene. Am. J. Hum. Genet., 63: 1307-15 (1998).
Spranger, International classification of osteochondrodysplasias, Eur. J. Pediatr., 151: 407-15 (1992).
Staehling-Hampton, et al., "A 52-kb Deletion in the SOST-MEOX1 Intergenic Region on 17q12-q21 Is Associated With van Buchem Disease in the Dutch Population", American Journal of Medical Genetics, vol. 110 (2002) 144-52.
Stanley et al., DAN is a secreted glyoopeotein related to Xenopus cerberus. Mech. Dev., 77: 173- 84 (1998).
Sudo et al., In vitro differentiation and calcification in a new clonal osteogenic cell line derived from newborn mouse calvaria, J. Cell Biol., 96: 191-8 (1983).
Sutcliffe, et al., "Antibodies That React with Predetermined Sites on Proteins", Science, vol. 219: 660-66 (1983).
Sutherland et al., Sclerostin promotes the apoptosis of human osteoblastic cells: A novel regulation of bone formation. Bone, 35: 828-35 (2004).

(56) References Cited

OTHER PUBLICATIONS

Suzawa et al., Extracellular matrix-associated bone morphogenetic proteins are essential for differentiation of murine osteoblastic cells in vitro. Endocrinology, 140: 2125-33 (1999).
Tam, et al., "TGF-β Receptor Expression on Human Keratinocytes: A 150 kDa GPI-Anchored TGF-131 Binding Protein Forms a Heteromeric Complex With Type I and Type II Receptors", J_ Cellular Biochemistry, vol. 70, No. 4 (1998) 573-586.
Ten Dijke et al., "Osteocyte-Derived Sclerostin Inhibits Bone Formation: Its Role in Bone Morphogenetic Protein and Wnt Signaling" J. Bone Joint Surg. Am., vol. 90, 31-35 (2008).
Thompson et al., Affinity maturation of a high-affinity human monoclonal antibody against the third hypervariable loop of human immunodeficiency virus: Use of phage display to improve affinity and broaden strain reactivity. J. Mol. Biol., 256: 7-88 (1996).
Thornton et al., Prediction of progress at last. Nature, 354: 105-6 (1991).
Tian et al., Treatment with a sclerostin antibody increases cancellous bone formation and bone mass regardless of marrow composition in adult female rats, Bone 47: 529-533 (2010).
Tian, et al., "Sclerostin antibody increases bone mass by stimulating bone formation and inhibiting bone resorption in a hindlimb-immobolized rat model" Bone, 48(2): 197-201 (2011).
Tjaderhane et al., A high sucrose diet decreases the mechanical strength of bones in growing rats. J. Nutr., 128: 1807-10 (1998).
Uitterlinden et al., Relation of alleles of the collagen type lα1 gene to bone density and the risk of osteoporotic fractures in postmenopausal women. New Engl. J. Med., 338: 1016-21 (1998).
Utting et al., Hypoxia stimulates osteoclast formation from human peripheral blood. Cell Biochem. Funct., 28: 374-80 (2010).
Valero et al., Quaternary structure of casein kinase 2. J. Biol. Chem., 27(14): 8345-52 (1995).
Van Bezooijen et al., "Wnt but Not BMP Signaling Is Involved in the Inhibitory Action of Sclerostin on BMP-Stimulated Bone Formation" J. Bone Miner. Res., vol. 22, No. 1, 19-28 (2007).
Van Bezooijen, et al., "Sclerostin Is an Osteocyte-expressed Negative Regulator of Bone Formation, But Not a Classical BMP Antagonist" J. Exp. Med., vol. 199, No. 6, 805-14, (2004).
Van Bezooijen, et al., "SOST/sclerostin, an osteocyte-derived negative regulator of bone formation", Cytokine and Growth Factor Reviews, vol. 16, No. 3 (2005) 319-27.
Van Hul, et al., "Van Buchem Disease (Hyperostosis Cortica is Genera isata) Maps to Chromosome 17q12-q21", Am. J, Hum. Genet., vol. 2 (1998) 391-99.
Vanier, et al., "Recent Advances in Elucidating Niemann-Pick C Disease", Brain Pathology, vol. 8 (1998) 163-74.
Veverka, et al., "Characterization of the Structural Features and Interactions of Sclerostin", J Biol Chem, vol. 284, No. 16 (2009) 10890 900.
Viter et al., Analysis of antigenic structure of potato virus M Ukrainian strains. Biopolimery I Kletka, Naukova Dumka, Kiev K, UK, 16: 312-9 (2000).
Von Bubnoff et al., Intracellular BMP signaling regulation in vertebrates: Pathway or network? Dev. Biol., 239: 1-14 (2001).
Wall, Transgenic livestock: Progress and prospects for the future. Theriogenology, 45: 57-68 (1996).
Wang et al., IFP 35 forms complexes with B-ATF, a member of the AP1 family of transcription factors. Biochem. Biophys. Res. Commun., 229: 316-22 (1996).
Warmington, et al., "Sclerostin antagonism in adult rodents, via monoclonal antibody mediated blockate, increases bone mineral density and implicates sclerostin as a key regulator of bone mass during adulthood", Journal of Bone and Mineral Research, vol. 19 (2004) S56-7.
Warmington, K., et al. "Sclerostin Monoclonal Antibody Treatment of Osteoporotic Rats Completely Reverses One Year of Ovariectomy-Induced Systemic Bone Loss", Journal of Bone and Mineral Research, Sep. 2005, vol. 20, No. 9, Suppl. 1: p. S22.
Winkler et al., "Osteocyte control of bone formation via sclerostin, a novel BMP antagonist" EMBO J., vol. 22, No. 23, 6267-76 (2003).
Winkler et al., "Sclerostin Inhibition of Wnt-3a-induced C3H10T1/2 Cell Differentiation Is Indirect and Mediated by Bone Morphogenetic Proteins*" J. Biol. Chem., vol. 280, No. 4, 2498-502, (2005).
Winkler et al., Noggin and sclerostin bone morphogenetic protein antagonists form a mutually inhibitory complex. J. Biol. Chem., 279(35): 36296-8 (2004).
Winter et al., Making antibodies by phage display technology. Annu. Rev. Immunol., 12: 433-55 (1994).
Wolff et al., Monoclonal antibody homodimers: Enhanced antitumor activity in nude mice. Cancer Res., 53: 2560-5 (1993).
Yanagita, "BMP antagonists: their roles in development and involvement in pathophysiology", Cytokine Growth Factor Rev., 16(3): 309-17 (2005).
Yanagita, "Modulator of bone morphogenic protein activity in the progression of kidney diseases", Kidney Int., 70(6): 989-93 (2006).
Yanagita, et al., "USAG-1: a bone morphogenic protein antagonist abundantly expressed in the kidney", Biochem. Biophys. Res. Commun., vol. 316, No. 2 (2004) 490-500.
Yanagita, et al., "Uterine sensitization-associated gene-1 (USAG-1), a novel antagonist expressed in the kidney, accelerates tubular injury", J. Clin. Invest., 116(1): 70-9 (2005).
Yang et al., CDR walking mutagenesis for the affinity maturation of a potent human Anti-HIV-1 antibody into the bicomolar range. J. Mol. Biol., 254: 392-403 (1995).
Yates et al., Inhibition of bone resorption by inorganic phosphate in mediated by both reduced osteoclast formation and decreased activity of mature osteoclasts. J. Bone Miner. Res., 6(5): 476-8 (1990).
Yoda, et al., "Review of Bone Union Evaluation Time by E-mail Questionnaire", Orthopeedic Surgery and Traumatology, 59(3): 61-18 (2010).
Yoshida et al., Osteoinduction capability of recombinant human bone morphogenetic protein-2 in intramuscular and subcutaneous sites: An experimental study. J. Cranio-Maxillofac. Surg., 26: 112-5 (1998).
Zambaux et al., Influence of experimental parameters on the characteristics of poly(lactic acid) nanoparticles prepared by a double emulsion method. J. Controlled Rel., 50(1-3): 31-40 (1998).
Zhang et al., Humanization of an anti-human TNF-β antibody by variable region resurfacing with the aid of molecular modeling. Molec. Immunol., 42(12): 1445-51 (2005).
Zimmerman et al., The spemann organizer signal noggin binds and inactives bone morphogenetic protein 4. Cell, 86 (4):599-606 (1996).
Zlotogora et al., Dominance and homozygosity, Am. J. Med. Genet., 68: 412-6 (1997).
Zur Muhlen et al., Solid lipid nanoparticles (SLN) for controlled drug delivery—Drug release and release mechanism. Eur. J. Pharm. Biopharm., 45(2):149-55 (1998).
Amgen press release "Amgen Presents Denosumab and Sclerostin Antibody Data at American Society for Bone and Mineral Research Annual Meeting; Data Suggest the Potential for Targeting the Key Proteins, RANK Ligand and Sclerostin, for Bone Loss Conditions" (Sep. 19, 2006).
Baron et al. "Targeting the Wnt/beta-catenin pathway to regulate bone formation in the adult skeleton," Endocrinology, 2007, 148(6):2635-43.
Bilezikian et al. "Combination/sequential therapies for anabolic and antiresorptive skeletal agents for osteoporosis," Curr Osteoporos Rep., 2006, 4(1):5-13.
Black et al. "One year of alendronate after one year of parathyroid hormone (1-84) for osteoporosis," N Engl J Med, 2005, 353(6):555-65.
Camacho et al. "Postmenopausal osteoporosis: an update on current and future therapeutic options," Expert Rev Endocrinol Metab., 2007, 2(1):79-90.
Canalis et al. "Mechanisms of anabolic therapies for osteoporosis," N Engl J Med., 2007, 357(9):905-16.
Complaint filed by Ossifi-Mab LLC in respect of EP 3345607 in the Dusseldorf Regional Court on Apr. 4, 2023.
Applicant's letter of Jan. 11, 2019 filed on EP 18157578.8.

(56) References Cited

OTHER PUBLICATIONS

Datasheet for Antibody "1A12" commercially available from Abcam.
Decision of OD of Jun. 25, 2021 for patent EP2144613B1.
Excerpt from Bone health and osteoporosis : a report of the Surgeon General. Rockville, Md. : U.S. Dept. of Health and Human Services, Public Health Service, Office of the Surgeon General; Washington, D.C .; p. 77; 2004.
Excerpt from the textbook "The Merck Manual" ( 19th edition, Whitehouse Station, New Jersey/USA 2006; pp. 305-308 chapter "Osteoporosis").
Excerpt from the textbook Mutschler (8th edition, Wissenschaftliche Verlagsgesellschaft, Stuttgart 2001, pp. 395-396).
Excerpt from the textbook Mutschler (9th edition, Wissenschaftliche Verlagsgesellschaft, Stuttgart 2008, pp. 395-401).
Grey et al. "Emerging and potential therapies for osteoporosis," Expert Opin Investig Drugs, 2005, 14(3):265-78.
Hodsman et al. "Parathyroid hormone and teriparatide for the treatment of osteoporosis: a review of the evidence and suggested guidelines for its use," Endocr Rev., 2005, 26(5):688-703.
Infringement action filed by Patentee against Opponents on Apr. 24, 2023.
Keller et al. "SOST is a target gene for PTH in bone," Bone, 2005, 37(2):148-58.
Khan et al. "Anabolic agents: a new chapter in the management of osteoporosis," J Obstet Gynaecol Can., 2006, 28(2):136-41.
Krishnan et al. "Regulation of bone mass by Wnt signaling," J Clin Invest., 2006, 116(5):1202-9.
McClung et al. "Effects of 24 Months of Treatment With Romosozumab Followed by 12 Months of Denosumab or Placebo in Postmenopausal Women With Low Bone Mineral Density: A Randomized, Double-Blind, Phase 2, Parallel Group Study," J Bone Miner Res., 2018, 33(8):1397-1406.
New York State Osteoporosis Prevention and Education Program (NYSOPEP) guidance document (Jun. 2020).
Opposition filed against the grant of European patent EP3345607B1 on behalf of Amgen Europe B.V. on Jul. 26, 2023. 56 pages.
Opposition filed against the grant of European patent EP3345607B1 on behalf of Hightone Management Limited. 10 pages.
Opposition filed against the grant of European patent EP3345607B1 on behalf of J A Kemp LLP on Jul. 26, 2023. 52 pages.
Opposition filed against the grant of European patent EP3345607B1 on behalf of UCB Pharma CmbH and UCB Pharma S.A. on Jul. 26, 2023. 38 pages.
Ott. "Sclerostin and Wnt signaling—the pathway to bone strength," J Clin Endocrinol Metab., 2005, 90(12):6741-3.
Poole et al. "Parathyroid hormone—a bone anabolic and catabolic agent," Curr Opin Pharmacol., 2005, 5(6):612-7.
Priority filing U.S. Appl. No. 60/882,642, filed Dec. 29, 2006.
Proof of Publication date (Camacho et al. "Postmenopausal osteoporosis: an update on current and future therapeutic options," Expert Rev Endocrinol Metab., 2007, 2(1):79-90).
Proof of publication date (Lewiecki, "Rank ligand inhibition with denosumab for the management of osteoporosis" Expert Opin. Biol. Ther., vol. 6, No. 10, pp. 1041-1050 (2006)).
Request for grant form for EP 18157578.8.
Rittmaster et al. "Enhancement of bone mass in osteoporotic women with parathyroid hormone followed by alendronate," J Clin Endocrinol Metab., 2000, 85(6):2129-34.
Rosen et al. "Clinical review 123: Anabolic therapy for osteoporosis," J Clin Endocrinol Metab., 2001, 86(3):957-64.
Russell et al. "Bone biology and the pathogenesis of osteoporosis," Curr Opin Rheumatol., 2006, 18 Suppl 1:S3-10.
Schipani et al. "Meeting Report from the 27th Annual Meeting of the American Society for Bone and Mineral Research," BoneKEy-Osteovision, 2006, 3(1)-29-62.
Shoback. "Update in Osteoporosis and Metabolic Bone Disorders," J Clin Endocrinol Metab, 2007, 92(3):747-753.
Submission dated Jun. 11, 2021 filed by applicant during examination of EP3345607B1.
Van Bezooijen et al. "Bone morphogenetic proteins and their antagonists: the sclerostin paradigm," J Endocrinol Invest, 2005, 28(8 Suppl):15-7.
Warmington et al. J Bone Miner. Res. 19, S56 (2004).

\* cited by examiner

1

METHODS OF ALTERING BONE GROWTH BY ADMINISTRATION OF SOST OR WISE ANTAGONIST OR AGONIST

This application is a divisional of application Ser. No. 15/269,022 filed Sep. 19, 2016 (now U.S. Pat. No. 11,608,373 issued Mar. 21, 2023), which in turn is a continuation of application Ser. No. 14/504,544 filed Oct. 2, 2014 (now abandoned), which in turn is a continuation of application Ser. No. 13/796,530 filed Mar. 12, 2013 (now U.S. Pat. No. 8,877,196 issued Nov. 4, 2014), which in turn is a divisional of Ser. No. 13/420,846 filed Mar. 15, 2012 (now abandoned), which in turn is a continuation of application Ser. No. 11/962,522 filed Dec. 21, 2007 (now U.S. Pat. No. 8,178,099 issued May 15, 2012), which in turn is a nonprovisional of provisional application No. 60/882,642 filed Dec. 29, 2006.

BACKGROUND OF THE INVENTION

1. Field of the Invention

The present invention relates to methods of altering bone growth. In particular, the present invention relates to promoting local bone growth by administering therapeutic amounts of a Sclerostin (hereinafter sometimes "Sost") or Wise antagonist with or without an osteoconductive scaffold to a mammal. In a different embodiment, the present invention relates to implantable medical devices comprising Sost or Wise antagonists or agonists. In a different embodiment, the present invention relates to promoting new bone by systemic administration of a Sost or Wise antagonist in combination with an antiresorptive agent. In another embodiment, the present invention relates to methods of reducing bone both systemically and locally by administering a therapeutic amount of a Sost or Wise agonist to a mammal. In a still further embodiment, the present invention relates to a method of protecting a mammalian kidney from any chemical injury or glomuleronephritis by administering a Wise or Sost antagonist.

2. Brief Description of the Background Art it is well-understood that bone formation is indicated for treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc. Contrarywise, it is also understood that more rarely disorders appear in mammals wherein bone is overproduced such as in: heterotopic ossification or osteosarcoma treatment, to prevent progression or reduce spinal stenosis of osseous origin such as osteophyte or ossification of the posterior longitudinal ligament, to prevent spontaneous fusion or arthrodesis with joint or disc arthroplasty, to prevent or treat spontaneous spinal fusion such as diffuse idiopathic skeletal hyperostosis and ankylosing spondylitis, preventing ossification or calcification of ligaments, tendons or joint capsules, treating heterotopic bone formation, preventing systemic hyperostosis resulting from metabolic bone disease, and Paget's disease. For these indications and others it is desired to reduce or inhibit such overproduction when possible.

Increasing bone mineralization to treat conditions characterized at least in part by increased bone resorption, such as osteopenia, bone fractures, osteoporosis, arthritis, tumor metastases., Paget's disease and other metabolic bone disorders, using cathepsin K inhibitors and TGF-beta binding proteins, etc., are well-known as shown by US patent application No. 20040235728 to Selwyn Aubrey Stoch, published Nov. 25, 2004, arid Mary E. Brunkow et al U.S. Pat No. 6,489,445 and US patent application publication 20040009535, published Jan. 15, 2004. In the Brunkow '535 and '445 publication, the TGF-beta binding proteins include Sost polypeptide (full length arid short peptide) antibodies that interfere with the interaction between the TGF-beta binding protein scierostin and a TGF-beta superfamily member, particularly a bone morphogenic protein. All of the diseases named above are due to a systemic loss of bone mineral and thus the administration of the antibody therapeutic is for systemic (whole body) increase in bone mineral density.

In the Brunkow '445 and '535 patent, the binding proteins preferably specifically to at least one human bone morphogenic protein (BMP) among BMP-5 and BMP-6.

U.S. Pat. No. 6,395,511 to Brunkow, et al. teaches a novel family of human TGF-beta binding proteins and nucleic acids encoding them. The protein binds to at least human bone morphogenic protein-5 and human bone morphogenic protein-6.

Sclerosteosis is a progressive sclerosing bone dysplasia. Sclerostin (the Sost gene) was originally identified as the sclerosteosis-causing gene. Sclerostin was intensely expressed in developing bones of mouse embryos. Punctuated expression of scierostin was localized on the surfaces of both intramembranously forming skull bones and endochondrally forming long bones. The physiological role of scierostin remains to be elucidated. However, it is known that loss of function mutations in Sost cause a rare bone dysplasia characterized by skeletal overgrowth.

In-San Kim's US patent application No. 20060165799, published Jul. 27, 2006, teaches a bone-filling composition for stimulating bone-forming and bone-consolidation comprising biocompatible calcium sulfate and viscous biopolymers. The composition is intended to be administered easily into the missing part of injured bone without diffusing to surrounding organs.

in Ronald S. Sapieszko's U.S. Pat. No. 5,939,039, issued in 1999 teaches the processes to yield unique calcium phosphate precursor minerals that can be used to form a self-setting cement or paste. Once placed in the body, these calcium phosphate cements (CPC) will be resorbed and remodeled (converted) to bone.

For example, calcium phosphate particles prepared in accordance with the '039 patent can be used in any of the orthopaedic or dental procedures known for the use of calcium phosphate; the procedures of bone filling defect repair, oncological defect filling, craniomaxillolacial void filling and reconstruction, dental extraction site filling.

US patent application No. 20060198863 to Carl Alexander DePaula, published Sep. 7, 2006, relates to a formable ceramic composition for filling bone defects. The composition comprises ceramic beta tricalcium phosphate particles having a particle size from about 40 microns to 500 microns admixed with a hydrogel carrier containing citric acid buffer. The composition has a pH between 7.0 to 7.8 and the hydrogel component of the carrier ranges from about 1.0 to 5.0% of the composition.

Wise and SOST are understood to be closely related family members (Ellies et al , JBMR 2006 November;21 (11):1738-49.). Those of ordinary skill are aware that the Wise null mutant mouse exhibits a bone phenotype (Keynote presentation at the 2005 American Society of Bone Mineral Research meeting in Nashville, TN. State of the Art lectures, an embryonic source of skeletal tissue. Patterning Craniofacial Development; by Robb Krumlauf, Ph.D., Stowers Institute for Medical Research, Kansas City, Missouri, USA US patent application No. 2005025604 to Vignery published Nov. 17, 2005 shows induction of bone formation by mechanically inducing an increase in osteoblast activity and elevating systemic blood concentration of a bone anabolic agent, including optionally elevating systemic blood concentration of an antiresorptive agent.

Finally, Yanagita, *Modulator of bone morphogenic protein activity in the progression of kidney diseases*, Kidney Int., Vol. 70, No. 6 (2006) 989-93 shows Usag-1 (also known as "Wise") protects the kidney from cisplatin insult due to BMB inhibition. See also Yanagita, *Uterine sensitization-associated gene-1 (USAG-1), a novel antagonist expressed in the kidney, accelerates tubular injury*, J. Clin. Invest., Vol. 116, No. 1 (2005) 70-9. Yanigita, *BMP antagonists: their roles in development and involvement in pathophysiology*, Cytokine Growth Factor Rev., Vol 16, No. 3 (2005) 309-17, and Yanagita, *USAG-1: a bone morphogenic protein antagonist abundantly expressed in the kidney*, Biochem. Biophys. Res. Commun., Vol, 316, No. 2 (2004) 490-500 and

SUMMARY OF THE INVENTION

It is an object of the present invention to provide a method of promoting local bone growth, comprising the steps of administering locally a therapeutic amount of a Sost antagonist to a mammalian patient in need thereof.

It is an object of the present invention to provide a method of promoting local bone growth, comprising the steps of administering locally a therapeutic amount of a Wise antagonist to a mammalian patient in need thereof.

It is an object of the present invention to provide a method of promoting local hone growth, comprising the steps of administering locally a therapeutic amount of a Sost antagonist in conjunction with an osteoconductive biocompatible calcium salt scaffold to a mammalian patient in need thereof.

It is an object of the present invention to provide a method of promoting local bone growth, comprising the steps of administering locally a therapeutic amount of a Wise antagonist in conjunction with an osteoconductive biocompatible calcium salt scaffold to a mammalian patient in need thereof.

It is a further object of the present invention to provide a medical orthopedic or periodontal device, comprising a structural support, wherein an implantable portion of said structural support is adapted to he permanently implanted within a mammalian body, said implanted structure support being at least partially retained in said body by local bone growth, said structural support bearing an at least a partial external coating of a Sost antagonist with or without an osteoconductive biocompatible scaffold.

It is a further object of the present invention to provide a medical orthopedic or periodontal device, comprising a structural support, wherein an implantable portion of said structural support is adapted to be permanently implanted within a mammalian body, said implanted structure support being at least partially retained in said body by local bone growth, said structural support bearing an at least a partial external coating of a Wise antagonist with or without an osteoconductive biocompatible scaffold.

It is a still further object of the present invention to provide a method of increasing bone density bath systemically (whole body) and locally, comprising the steps of administering, to a mammalian patient in need thereof, a therapeutic amount of a Sost antagonist together with an antiresorptive drug.

It is a still further object of the present invention to provide a method of increasing bone density both systemically (whole body) and locally, comprising the steps of administering, to a mammalian patient in need thereof, a therapeutic amount of a Wise antagonist together with an antiresorptive drug.

It is a still further object of the present invention to provide a method of reducing bone both locally and systemically (whole body), comprising the steps of administering a therapeutic amount of a Sost agonist to a mammalian patient in need thereof.

It is a still further object of the present invention to provide a method of reducing bone both locally and systemically (whole body), comprising the steps of administering a therapeutic amount of a Wise agonist to a mammalian patient in need thereof.

Yet another object of the present invention lies in a method of protecting a mammalian kidney from chemical injury which results in for example glomuleronephritis, comprising administering systemically or locally, to a patient in need thereof, a therapeutic amount of a SOST or Wise antagonist.

These objects and others are provided by, novel processes utilizing administration of Sost antagonists or agonists to mammalian patients. In particular, Sost antibody antagonists or agonists administered locally with or without an osteoconductive matrix or in conjunction with an antiresorptive agent. Alternatively, a Sost antibody antagonists administered systemically (whole body) in conjunction with an antiresorptive. Desirable Sost antagonists function through LRP5 or LRP6, or comprises an antibody or FAB fragment recognizing any one of SEQ ID NOS: 1-23.

The above features and advantages are provided by the present invention which utilizes either a Sost or Wise antagonist or a Sost or Wise agonist to provide bone growth or depletion, respectively.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As disclosed herein, proteins, particularly antibodies, muteins, nucleic acid aptamers, and peptide that antagonize specific binding of SOST or WISE (Usag-1/ectodin/sostdc1) to their natural receptors may serve as "binding agents"and "SOST antagonists or agonists" or "WISE antagonists or agonists" of the present invention.

Those of ordinary skill in this art are able to determine the appropriate "therapeutically effective amount" for administering such agonists and antagonists, as well as methods and schedules for such administration The phrase "specifically (or selectively) binds" or when referring to an antibody interaction, "specifically (or selectively) immunoreactive with," refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antibodies bind to a particular protein sequence, thereby identifying its presence.

Specific binding to an antibody under such conditions requires an antibody that is selected for its specificity for a particular protein. For example, antibodies raised against a particular protein, polymorphic variants, alleles, orthologs, and conservatively modified variants, or splice variants, or portions thereof, can be selected to obtain only those polyclonal antibodies that are specifically immunoreactive with SOST, WISE or an LRP, preferably an LRP5 or LRP6 protein and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods for determining whether two molecules specifically interact are disclosed herein, and methods of determining binding affinity and specificity are well known in the art (see, fix example, Harlow and Lane, Antibodies: A laboratory manual (Cold Spring Harbor Laboratory Press, 1988); Friefelder, "Physical Biochemistry: Applications to biochemistry and molecular biology" (W. H. Freeman and Co. 1976)).

Furthermore, Sost or Wise can interfere with the specific binding of a receptor and its ligand by various mechanism, including, for example, by binding to the ligand binding site, thereby interfering with ligand binding; by binding to a site other than the ligand binding site of the receptor, but sterically interfering with ligand binding to the receptor; by binding the receptor and causing a conformational or other change in the receptor, which interferes with binding of the ligand; or by other mechanisms. Similarly, the agent can bind to or otherwise interact with the ligand to interfere with its specifically interacting with the receptor. For purposes of the methods disclosed herein, an understanding of the mechanism by which the interference occurs is not required and no mechanism of action is proposed. A Wise or Sost binding agent, such as an anti-Wise or anti-Sost antibody, or antigen binding fragment thereof, is characterized by having specific binding activity ($K_a$) of at least about $10^5$ $M^{-1}$, $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, Ann. NY Acad. Sci. 51: 660-72, 1949).

The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, IL). See also, e.g., Kuby, J., Immunology, 3rd Ed., W. H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

The term "antibody" includes both polyclonal and monoclonal antibodies. The term also includes genetically engineered forms such as chimeric antibodies (e.g., humanized murine antibodies) and heteroconjugate antibodies (e.g., bispecific antibodies). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol :5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)). Humanization can be essentially performed following the method of Winter and co-workers (Jones et al., Nature 321:522-525 (1986); Riechrmann et al., Nature 332:323-3.27 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified. variant" where the alteration results in the substitution of an amino acid with a chemically similar amino acid. Conservative substitution tables providing functionally similar naturally occurring and non-naturally occurring amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspa.rtic acid (D), Glutamic acid (F); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (5), Threonine (T); and 8) Cysteine (C), Methionine (M) (see, e.g., Creighton, Proteins (1984)), "Homologous," in relation to two or more peptides, refers to two or more sequences or subsequences that have a specified percentage of amino acid residues that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI or the like). The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids in length, or more preferably over a region that is 50-100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acari. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et at, eds. 1995 supplement)).

Preferred examples of algorithms that are suitable for determining percent sequence identity and sequence similarity include the BLAST and BLAST 2.0 algorithms, which are described in Altschul et al., Nue. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPS containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a peptide is considered similar to a reference sequence if the smallest sum probability in a comparison of the test peptide to the reference peptide is less than about 0.2, more preferably less than about 0.01, and most preferably less than about 0.001. Log values may be large negative numbers, e.g., 5, 10, 20, 30, 40, 40, 70, 90, 110, 150, 170, etc.

DETAILED DESCRIPTION OF THE INVENTION

The present invention is directed to methods for promoting local bone deposition in mammals using materials that antagonize Sost proteins. Suitable antagonists may be provided by blocking antibodies. Antibodies include those that specifically bind to any of Sost agonist proteins according to SEQ ID NOS: 1-23 or homologs that are >75% identity and more preferable antibodies are monoclonal and/or humanized antibodies. It is similarly desirable that the antagonist operates through LRP5 or LRP6. The antagonist may be coadministered or serially administered with an antiresorptive drug if desired to increase or hasten bone formation. For example, the antiresorptive drug may be a bisphosphonate (i.e. fosamax, actonel), a PTH or analog (i.e. Forteo), calcitonin or analog (i.e. Miacalcic), Vitamin D or analog, SERM or analog (i.e. Evista), These blocking Sost-recognizing antibodies may be made readily by those of ordinary skill in this art by conventional techniques. Preferably, these antibodies will be FAB fragments or monoclonal antibodies, and more preferably, the FAB fragments or monoclonal antibodies will be humanized. Suitable humanized monoclonal antibodies have been created by Amgen, for example. Stowers Institute also provides suitable blocking antibodies designated 4G10, 4B9 and 6E6. Another suitable blocking antibody is 1A12 commercially available from Abcam.

The present invention is directed to methods for reducing bone in mammals using materials that agonize Sost or Wise proteins, by administering to a mammal a peptide that recognizes any of SEQ ID NOS: 1-23. Peptides for treating systemic (whole body) low bone mass diseases are taught in Applicant's U.S. patent application Ser. No. 11/508,701 (U.S. publication No. 20070292444) and in Applicant's US patent application publication No. 20040023356. All subject matter of both the 11/508,701 and 11/613,658 (U.S. publication No. 20070298038) applications and the 20040023356publication is hereby incorporated by reference.

The present invention is directed to methods for protecting mammalian kidneys from any chemical injury that causes renal damage, for example glomuleronephritis, by administering to a mammal a Sost or Wise antagonist. Such subject matter is disclosed in the 11/508,701 and 11/613,658 applications and the 20040023356 publication, incorporated by reference.

Other aspects of the present invention are directed towards medical implants. Such medical devices and implants include, for example, the osteogenic devices and methods of using the same for repairing endochondral bone and osteochondral defects taught in US patent application publication No. 20060177475 to David Rueger et al, published Aug. 10, 2006, as well as in issued U.S. Patent and published application Nos. 6,190,880, 20020169122, 20020187104, 20060252724, 20070172479, 5,344,654, 5,324,819, 5,468,845, 6,949,251, 6,426,332 and 5,656,593, the subject matter of which is hereby incorporated by reference.

These medical devices generally provide a structural support having an implantable portion preferentially adapted to mechanically engage bone and/or cartilage as taught, for instance, in US patent application publication No. 20060178752 to Joseph Vaccarino III, et al, published Aug. 10, 2006, the subject matter of which is hereby incorporated by reference. These bone implants desirably comprise an active agent on at least a portion thereof. As shown by US patent application publication No. 20060188542 to John Dennis Bobyn, et al, published Aug. 24, 2006, the subject matter of which is hereby incorporated by reference, the active agent is preferably formulated to he locally deliverable to bone proximate the implant in sustained-release or in at least a two-phased release scheme. In the latter, a first phase rapidly releases a first quantity of the active agent, and the second and subsequent phases gradually release a second quantity of the active agent, whereby bone formation stimulated by the active agent is modulated.

Medical devices such as bone implants feature implantable portions bearing Sost antagonists foster quicker and more complete bone formation in situ. The implantable portion of the medical device may be desirable at least partially or totally covered or impregnated with a Sost antagonist. It has believed to be helpful to produce the implantable portion of the medical device from a matrix material in which bone can be formed, to increase permanently retaining the same. This is thought to be desirable for materials such as teeth and artificial bone graft sections, and the like. Alternatively, when the implantable sections are load bearing and formed, e.g., of stainless steel, these implantable sections are desirable formed with a Sost antagonist coating. In that event, it is desirable to also provide a separate matrix material conducive to forming new bone growth.

Suitable matrixes include those comprising composite biomaterials having a sponge-like structure such as those containing, e.g., phosphophoryn and/or collagen as taught in Takashi Saito's US patent application publication No. 20060188544, published Aug. 24, 2006, the subject matter of which is hereby incorporated by reference. Such coatings include, for example, the single and multilayer coatings taught in US patent application publication No. 20060204542 to Zongtao Zhang et al, published Sep. 14, 2006, as well as those in U.S. Pat. Nos. 6,949,251, 5,298, 852, 5,939,039, and 7,189,263 and may be made by conventional methods including the methods taught therein, the subject matter of which is hereby incorporated by reference.

Usag-1 (Wise) may be functioning through the Wnt pathway for its role in renal protection. For this reason and others, a therapeutic amount of a Wise antagonist may he administered to a mammalian patient in need thereof so as to protect a kidney from renal damage for example glomuleronephritis. In particular, it is especially preferred to administer such Wise or Sost blocking antibodies so as to protect the mammalian kidney from external insult engendered from disease or chemicals, such as toxins or drug therapy.

The present invention also contemplates agents that antagonize binding of SOST and/or WISE to its native receptor(s) ("SOST antagonist"). SOST antagonist include a peptidomimetic, which is an organic molecule that mimics the structure of a peptide; or a peptoid such as a vinylogous peptoid.

The present invention also contemplates agents that agonize binding of SOST and/or WISE to its native receptor(s) ("SOST agonists). SOST or Wise agonists include a peptidomimetic, which is an organic molecule that mimics the structure of a peptide; or a peptoid such as a vinylogous peptoid.

Preferred embodiments of the present invention include SOST antagonists that are preferably SOST antibodies, WISE antibodies or LRP antibodies, although the invention also contemplates inhibitory peptides and small molecular inhibitors as described above. Antibodies of the invention are preferably chimeric, more preferably humanized antibodies, ideally monoclonal antibodies preferably raised against murine proteins, most preferably murine SOST.

SOST, WISE, or LRP antagonist antibodies, including anti-SOST antibodies, may be raised using as an immunogen, such as a substantially purified full length protein, such as murine SOST, but may also be a SOST, WISE or LRP protein of human, mouse or other mammalian origin. The immunogen may, be prepared from natural sources or produced recombinantly, or a peptide portion of a protein, which can include a portion of the cystiene knot domain, for example, a synthetic peptide. A non-immunogenic peptide may be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane (supra, 1988).

Particularly useful antibodies for performing methods of the invention are monoclonal antibodies that that specifically bind to LRP molecules, WISE or, most preferably, SOST. Such antibodies are particularly useful where they bind SOST with at least an order of magnitude greater affinity than they bind another protein. Methods for creating chimeric antibodies, including humanized antibodies, is discussed in greater detail below.

1. Production of Recombinant Antibody

Methods for producing both monoclonal and polyclonal antibodies from identified proteins or peptides are well known in the art. In order to prepare recombinant chimeric and humanized antibodies that may function as SOST antagonists of the present invention, the nucleic acid encoding non-human antibodies must first be isolated. This is typically done by immunizing an animal, for example a mouse, with prepared Sost or Wise or an antigenic peptide derived therefrom. Typically mice are immunized twice intraperitoneally with approximately 50 micrograms of protein antibody per mouse. Sera from immunized mice can be tested for antibody activity by immunohistology or immunocytology on any host system expressing such polypeptide and by ELISA with the expressed polypeptide. For immunohistology, active antibodies of the present invention can be identified using a biotinconitrgated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays common to those of skill in the art, for example, Western blot analysis.

The nucleic acids encoding the desired antibody chains can then be isolated by, for example, using hybridoma mRNA or splenic mRNA as a template for PCR amplification of the heavy and light chain genes [Huse, et al., Science 246:1276 (1989)]. Nucleic acids for producing both antibodies and intrabodies can be derived from murine monoclonal hybridomas using this technique [Richardson J. H., et al., Proc Natl Acad Sci USA 92:3137-3141 (1995); Biocca S., et al., Biochem and Biophys Res Comm, 197:422-427 (1993) Mhashilkar, A. M., et al., EMBO J 14:1542-1551 (1995)]. These hybridomas rovide a reliable source of well-characterized reagents for the construction of antibodies and are particularly useful once their epitope reactivity and affinity has been characterized. Isolation of nucleic acids from isolated cells is discussed further in Clackson, T., et al., Nature 352:624-628 (1991) (spleen) and Portolano, S., et al., supra: Barbas, C. F., et al., supra; Marks, J. D., et al., supra; Barbas, C. F., et al., Proc Natl Acad Sci USA 88:7978-7982 (1991) (human peripheral blood lymphocytes). Humanized antibodies optimally include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Strict. Biol., 2:593-596 (1992)].

A number of methods have been described to produce recombinant antibodies, both chimeric and humanized. Controlled rearrangement of antibody domains joined through protein disulfide bonds to form chimeric antibodies may be utilized (Konieczny et al., Haematologia, 14(1):95-99, 1981). Recombinant DNA technology can also be used to construct gene fusions between DNA sequences encoding mouse antibody variable light and heavy chain domains and human antibody light and heavy chain constant domains (Morrison et al., Proc. Natl. Acad. Sci. USA, 81(21):6851-6855, 1984).

DNA sequences encoding the antigen binding portions or complementarity determining regions (CDR's) of murine monoclonal antibodies may be grafted by molecular means into the DNA sequences encoding the frameworks of human antibody heavy and light chains (Jones et al., Nature, 321 (6069):522-525, 1986; Riechmann et al., Nature, 332(6162): 323-327, 1988.). The expressed recombinant products are called "reshaped" or humanized antibodies, and comprise the framework of a human antibody light or heavy chain and the antigen recognition portions, CDR's, of a murine monoclonal antibody.

Other methods for producing humanized antibodies are described in U.S. Pat. Nos. 5,693,769; 5,693,761; 5,585, 089; 5,639,641; 5,565,332; 5,733,743; 5,750,078; 5,502, 167; 5,705,154; 5,770,403; 5,698,417; 5,693,493; 5,558, 864; 4,935,496; 4,816,567; and 5,530,101, each incorporated herein by reference in their entirety.

Techniques described for the production of single chain antibodies (U.S. Pat. No. 4,946,778, which is incorporated by reference) can he adapted to produce single chain humanized antibodies to Sost or Wise.

2. Purification of Recombinant Antibody

Affinity purification of an antibody pool or sera provides a practitioner with a more uniform reagent. Methods for enriching antibody granulation inhibitors using antibody affinity matrices to form an affinity column are well known in the art and available commercially (AntibodyShop, c/o Statens Serum Institut, Artillerivej 5, Bldg. P2, DK-2300 Copenhagen S). Briefly, an antibody affinity matrix is attached to an affinity support (see e.g.; CNBR Sepharose (R), Pharmacia Biotech). A mixture comprising antibodies is then passed over the affinity matrix, to which the antibodies bind. Bound antibodies are released by techniques common to those familiar with the art; yielding a concentrated antibody pool. The enriched antibody pool can then be used for further immunological studies, some of which are described herein by way of example.

Another approach uses recombinant bacteriophage to produce large libraries. Using the "phage method" (Scott and Smith, Science 249:386-390, 1990; Cwirla, et al, Proc. Natl. Acad. Sci., 87:6378-6382, 1990; Devlin et al., Science, 49:404-406, 1990), very large libraries can be constructed (106-108 chemical entities). A second approach uses primarily chemical methods, of which the Geysen method (Geysen et al., Molecular Immunology 23:709-715, 1986; Geysen et al. J. Immunologic Method 102:259-274, 1987; and the method of Fodor et al. (Science 251:767-773, 1991) are examples Furka et al. (14th international Congress of Biochemistry, Volume #5, Abstract FR:013, 1988; Furka, Int. J. Peptide Protein Res. 37:487-493, 1991), Houghton (U.S. Pat. No. 4,631,211; issued December 1986) and Rutter et al. (U.S. Pat. No. 5,010,175, issued Apr. 23, 1991) describe methods to produce a mixture of peptides that can be tested as agonists or antagonists.

3. Identification of Sost Antagonists

The present invention provides methods for identifying diagnostic and therapeutic SOST antagonists. Several exemplary methods for identifying such antagonists are described herein, including cell-based and in vitro techniques. A general method of identifying SOST antagonists involves evaluating the effects of antagonist candidates on bone deposition under controlled conditions. Preferably bone deposition is determined using micro-CT techniques on live animals. Preferred animals include rodents, more preferred are primates. Femur and vertebrae bones are particularly useful subjects for such study.

Briefly, the test animal is treated with a predetermined dose of a SOST antagonist candidate. A control animal is treated with a control solution, preferably a non-irritating buffer solution or other carrier.

It also has been found that successful implantation of the osteogenic factors for endochondral bone formation requires association of the proteins with a suitable carrier material capable of maintaining the proteins at an in vivo site of application. The carrier should be biocompatible, in vivo biodegradable and porous enough to allow cell infiltration.

The proteins of this invention, including fragments thereof, also may be used to raise monoclonal or polyclonal antibodies capable of binding specifically to an epitope of Sost, Wise, or LRP. These antibodies may be used, for example, in Sost or Wise antagonists or agonists purification protocols.

The Sost or Wise antagonists or agonists are useful in clinical applications in conjunction with a suitable delivery or support system (matrix). As disclosed herein, the matrix may be combined with Sost or Wise antagonists or agonists to induce endochondral bone formation reliably and reproducibly in a mammalian body. The matrix is made up of particles of porous materials. The pores must be of a dimension to permit progenitor cell migration into the matrix and subsequent differentiation and proliferation. The particle size should be within the range of 70 um-850 um, preferably 70 um-420 um, most preferably 150 um-420 um. It may be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation. Useful matrix materials comprise, for example, collagen; homopolymers or copolymers of glycolic acid, lactic acid, and butyric acid, including derivatives thereof; and ceramics, such as hydroxyapatite, tricalcium phosphate and other calcium phosphates. Combinations of these matrix materials also may be useful.

When the SOST antagonist candidate is delivered in a carrier, the control solution is ideally the carrier absent the SOST antagonist candidate. Multiple doses of the SOST antagonist candidate may be applied to the test animal, preferably following a predetermined schedule of dosing. The dosing schedule may be over a period of days, more preferably over a period of weeks.

Once the dosing schedule has been completed, both test and control animals are examined to determine the level of bone deposition present. This may be accomplished by any suitable method, but is preferably performed on live animals using x-ray equipment. Methods for micro-CT examination of bones in animals are well known in the art. A SOST antagonist candidate suitable for use as a SOST antagonist is identified by noting significant bone deposition in the test animal when compared to the control animal. Ideally bone deposition in the test bone(s) of the test animal should be at least 10%, more preferably 20%, most preferably 30% or 40% or more bone deposition than is present in the same bones of the control animal. Where necessary, levels of bone deposition may be calculated by determining the volume of bone deposition present in each animal. Calculations may be performed by constructing a 3-dimensional image of the bone deposition and calculating the volume from the image with the aid of e.g., histomorphometry.

In an exemplary embodiment, localized injection in situ of a SOST antagonist candidate, for example a monoclonal antibody described herein, may be made into a test animal, with a control animal receiving an equal volume of control solution without the SOST antagonist candidate. Identical dosing should be done on a weekly basis for four weeks. Suitable dosage will depend on the nature of the particular SOST antagonist candidate being tested. By way of example, in dosing it should he noted that systemic injection, either intravenously, subcutaneously or intramuscularly, may also be used. For systemic injection of a SOST antagonist candidate or a SOST antagonist or agonist, dosage should he about 5 mg/kg, preferably more preferably about 15 mg/kg, advantageously about 50 mg/kg, more advantageously about 100 mg/kg, acceptably about 200 mg/kg. dosing performed by nebulized inhalation, eye drops, or oral ingestion should be at an amount sufficient to produce blood levels of the SOST antagonist candidate similar to those reached using systemic injection. The amount of SOST antagonist candidate that must be delivered by nebulized inhalation, eye drops, or oral ingestion to attain these levels is dependent upon the nature of the inhibitor sed and can be determined by routine experimentation. It is expected that, for systemic injection of the monoclonal antibody SOST antagonist candidates described herein, therapeutic levels of the antibody may be detected in the blood one week after delivery of a 15 mg/kg dose.

SOST antagonists may also be identified using a process known as computer, or molecular modeling, which allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. rediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et. al., Acta Pharmaceutica Fennica 97, 159-166 (1988); Ripka, New Scientist 54-57 (Jun. 16, 1988); McKinaly and Rossmann, Annu. Rev. Pharmacol. Toxiciol. 29, 111-122 (1989);

Perry and Davies, OSAR: Quantitative Structure-Activity Relationships in Drug Design pp. 189-193 (Alan R. Liss, Inc. 1989); Lewis and Dean, Proc. R. Soc. Lond. 236, 25-140 and 141-162 (1989); and, with respect to a model receptor for nucleic acid components, Askew, et al., J. Am. Chem. Soc. 111, 1082-1090 (1989). Askew et al. constructed a new molecular shape which permitted both hydrogen bonding and aromatic stacking forces to act simultaneously. Askew et al. used Kemp's triacid (Kemp et al., J. Org. Chem. 46:5140-5143 (1981)) in which a U-shaped (diaxial) relationship exists between any two carboxyl functions. Conversion of the triacid to the imide acid chloride gave an acylating agent that could be attached via amide or ester linkages to practically any available aromatic surface. The resulting structure featured an aromatic plane that could be roughly parallel to that of the atoms in the imide function; hydrogen bonding and stacking forces converged from perpendicular directions to provide a microenvironment complimentary to adenine derivatives.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified.

4. Screening Compound Libraries

Whether identified from existing SOST antagonists or from molecular modelling techniques, SOST antagonists generally must be modified further to enhance their therapeutic usefulness. This is typically done by creating large libraries of compounds related to the SOST antagonist, or compounds synthesized randomly, based around a core structure. In order to efficiently screen large and/or diverse libraries of SOST antagonist candidates, a high throughput screening method is necessary to at least decrease the number of candidate compounds to be screened using the assays described above. High throughput screening methods involve providing a combinatorial chemical or peptide library containing a large number of potential therapeutic compounds (potential modulator or ligand compounds). Such "combinatorial chemical libraries" or "candidate libraries" are then screened in one or more assays, as described below, to identify those library members (particular chemical species or subclasses) that are able to promote bone deposition. The compounds thus identified can serve as conventional "lead compounds" or can themselves be used as potential or actual therapeutics.

Accordingly, the present invention provides methods for high throughput screening of SOST antagonists candidates. The initial steps of these methods allow for the efficient and rapid identification of combinatorial library members that have a high probability of being SOST antagonists. These initial steps take advantage of the observation that SOST antagonists are also LRP or SOST binding agents. Any method that determines the ability of a member of the library, termed a binding candidate, to specifically bind to SOST, WISE or an LRP protein is suitable for this initial high throughput screening. For example, competitive and non-competitive ELISA-type assays known to one of ordinary skill in the art may be utilized.

Binding candidates that are found to bind SOST, WISE or an LRP protein with acceptable specificity, e.g,. with a $K_a$ for SOST, WISE or an LRP protein of at least about $10^5$ $M^{-1}$, $10^6$ $M^{-1}$ or greater, preferably $10^7$ $M^{-1}$ or greater, more preferably $10^8$ $M^{-1}$ or greater, and most preferably $10^9$ $M^{-1}$ or greater, are SOST antagonist candidates and are screened further, as described above, to determine their ability to promote bone deposition.

5. Therapeutic Applications

Individuals to be treated using methods of the present invention may be any mammal, for example local increase in bone may be used for fracture healing, fusion (arthrodesis), orthopedic reconstruction, and periodontal repair. Systemic increase in bone would be for treatment of low bone mass, i.e. osteoporosis. Bone reduction would be used to treat unwanted heterotopic bone formation, ossification of longitudinal ligament, ossification during cervical stenosis, or osteosarcoma. Such individuals include a dog, cat, horse, cow, or goat, particularly a commercially important animal or a domesticated animal, more particularly a human.

In therapeutic use SOST antagonists generally will be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the SOST antagonist, for example, whether the SOST antagonist is an antibody, a peptide or a nonpeptide.

A pharmaceutically acceptable carrier may include physiologically acceptable compounds that act, for example, to stabilize the SOST antagonist or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SOST antagonist and on its particular physio-chemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The pharmaceutical compositions of the present invention may be prepared for administration by a variety of different routes. In general, the type of carrier is selected based on the mode of administration. Pharmaceutical compositions may he formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The methods of the present invention include application of SOST antagonists in cocktails including other medicaments, for example, antibiotics, fungicides, and anti-inflammatory agents. Alternatively, the methods may comprise sequential dosing of an afflicted individual with a SOST antagonist and one or more additional medicaments to optimize a treatment regime. In such optimized regimes, the medicaments, including the granulation inhibitor may be applied in any sequence and in any combination.

The SOST, Wise, or LRP antagonists or agonists of the present invention may also be included in slow release formulations for prolonged treatment following a single dose. In one embodiment, the formulation is prepared in the form of microspheres. The microspheres may be prepared as a homogenous matrix of a SOST antagonist with a biodegradable controlled release material, with optional additional medicaments as the treatment requires. The microspheres are preferably prepared in sizes suitable for infiltration and/or injection, and injected systemically, or directly at the site of treatment.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The amount of SOST, Wise, or LRP antagonist or agonists administered to an individual will depend, in part, on the disease and/or extent of injury. Methods for determining an effective amount of an agent to administer for a diagnostic or a therapeutic procedure are well known in the art and include phase I, phase II and phase III clinical trials. Generally, an agent antagonist is administered in a dose of about 0.01 to 200 mg/kg body weight when administered systemically, and at a concentration of approximately 0.1-100 µM when administered directly to a wound site. The total amount of SOST antagonist or agonists can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular SOST antagonist required to provide an effective amount to a region or regions of injury depends on many factors including the age and general health of the subject as well as the route of administration, the number of treatments to be administered, and the nature of the SOST antagonist, including whether the SOST antagonist is an antibody, a peptide, or a nonpeptide molecule. In view of these factors, the skilled artisan would adjust the particular dose so as to obtain an effective amount for efficaciously promoting bone deposition for therapeutic purposes.

All publications and. patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

What is claimed is:

1. A method for increasing bone formation in a human subject being treated with a sclerostin-recognizing antibody, comprising administering an antiresorptive drug to the human subject.

2. The method of claim 1, wherein the method increases bone mineral density in the human subject.

3. The method of claim 1, wherein the method increases bone mass in the human subject.

4. The method of claim 1, wherein the method increases bone growth in the human subject.

5. The method of claim 1, wherein the antiresorptive drug is selected from the group consisting of: a bisphosphonate, a selective estrogen receptor modulator (SERM), calcitonin, Vitamin D, parathyroid hormone (PTH), a Rank antagonist, denosumab, and combinations thereof.

6. The method of claim 1, wherein the antiresorptive drug is Vitamin D.

7. The method of claim 1, wherein the antiresorptive drug is a bisphosphonate.

8. The method of claim 7, wherein the bisphosphonate is alendronate or risedronate.

9. The method of claim 7, wherein the bisphosphonate is alendronate.

10. The method of claim 1, wherein the administration of the antiresorptive drug results in increased bone formation in the human subject relative to bone formation prior to administration of the antiresorptive drug in the human subject.

11. The method of claim 1, wherein the administration of the antiresorptive drug results in increased bone formation relative to a different human subject not being treated with the antiresorptive drug.

12. The method of claim 1, wherein the antiresorptive drug is serially administered to the human subject.

13. The method of claim 1, wherein the human subject has osteoporosis.

14. The method of claim 1, wherein the human subject has low bone density.

15. The method of claim 1, wherein the human subject has low bone mineral density.

16. The method of claim 1, wherein the human subject has previously been treated with a prior antiresorptive drug.

17. The method of claim 16, wherein the prior antiresorptive drug is the same as the antiresorptive drug administered to the human subject.

18. The method of claim 16, wherein the prior antiresorptive drug is different from the antiresorptive drug administered to the human subject.

19. The method of claim 1, wherein the human subject is being treated with the sclerostin-recognizing antibody subcutaneously.

20. The method of claim 1, wherein the antibody is formulated in a pharmaceutical composition.

21. The method of claim 20, wherein the pharmaceutical composition comprises water and sucrose.

22. The method of claim 20, wherein the pharmaceutical composition comprises acetate.

23. The method of claim 20, wherein the pharmaceutical composition comprises water, sucrose, and acetate.

24. An improved method of treating a human subject being treated with a sclerostin-recognizing antibody to increase bone formation in the human subject, wherein the improvement comprises:

separate administration of a first antiresorptive drug at the same time as the treatment with the sclerostin-recognizing antibody; and separate administration of a second antiresorptive drug after the administration of the first antiresorptive drug.

25. The method of claim 24, wherein the first antiresorptive drug is Vitamin D.

26. The method of claim 24, wherein the second antiresorptive drug is alendronate.

27. A method for increasing bone formation in a human subject with low bone mineral density being treated with a humanized sclerostin-recognizing antibody and vitamin D, comprising administration of alendronate to the human subject.

28. The method of claim 27, wherein the alendronate is administered serially to the human subject.

29. A method for increasing bone mineral density in a human subject with low bone mass being treated with a sclerostin-recognizing antibody, comprising serially administering an antiresorptive drug to the human subject.

30. The method of claim 29, wherein the antiresorptive drug is alendronate.

* * * * *